(12) United States Patent
Stanton et al.

(10) Patent No.: US 10,874,359 B2
(45) Date of Patent: Dec. 29, 2020

(54) CASTER SYSTEM FOR MOBILE APPARATUS

(71) Applicant: MOBIUS IMAGING, LLC, Shirley, MA (US)

(72) Inventors: Russell Stanton, Lunenberg, MA (US); Eugene A. Gregerson, Bolton, MA (US)

(73) Assignee: MOBIUS IMAGING, LLC, Shirley, MA (US)

( * ) Notice: Subject to any disclaimer, the term of this patent is extended or adjusted under 35 U.S.C. 154(b) by 0 days.

(21) Appl. No.: 15/718,164

(22) Filed: Sep. 28, 2017

(65) Prior Publication Data

US 2018/0014795 A1 Jan. 18, 2018

Related U.S. Application Data

(63) Continuation of application No. 14/212,169, filed on Mar. 14, 2014, now Pat. No. 9,801,592.

(Continued)

(51) Int. Cl.
*A61B 5/055* (2006.01)
*B60B 33/06* (2006.01)
(Continued)

(52) U.S. Cl.
CPC .............. *A61B 6/035* (2013.01); *A61B 5/055* (2013.01); *A61B 6/4405* (2013.01);
(Continued)

(58) Field of Classification Search
CPC ....... B62B 5/049; B62B 5/0452; B62B 61/12; B62B 61/125; B62B 2202/12;
(Continued)

(56) References Cited

U.S. PATENT DOCUMENTS 3,637,233 A 1/1972 Hoppl et al.
4,043,403 A * 8/1977 Anderson .............. A01B 63/22
172/413

(Continued)

FOREIGN PATENT DOCUMENTS

EP 0395711 B1 3/1995
WO 2010078481 A1 7/2010
WO WO2014143890 A1 9/2014

OTHER PUBLICATIONS

TRUMPF Medizin Systeme GmbH & Co. KG of Puchheim, Germany "JUPITER system brochure" pp. 1-34, (Nov. 2008).

(Continued)

*Primary Examiner* — Emma K Frick
(74) *Attorney, Agent, or Firm* — Howard & Howard Attorneys PLLC

(57) ABSTRACT

A mobile imaging device includes a base having at least one caster, a first drive mechanism that moves the system in a transport mode and translates an imaging component relative to the base in a scan mode, and a second drive mechanism that extends caster relative to the base to raise the base off the ground in the transport mode, and retracts the caster relative to the base to lower the base to the ground in the scan mode. A caster system for a mobile apparatus includes a base containing a housing and a caster, attached to the base, the caster having a wheel defining a wheel axis and a swivel joint defining a swivel axis and a pivot point defining a pivot axis, wherein the caster pivots on the pivot axis as the caster is retracted into the housing and extended out of the housing.

13 Claims, 19 Drawing Sheets

Related U.S. Application Data

(60) Provisional application No. 61/791,509, filed on Mar. 15, 2013.

(51) Int. Cl.
  *A61B 6/03* (2006.01)
  *A61B 6/00* (2006.01)
  *B60T 1/14* (2006.01)

(52) U.S. Cl.
  CPC ........ *B60B 33/066* (2013.01); *B60B 2200/26* (2013.01); *B60T 1/14* (2013.01); *Y10T 16/182* (2015.01)

(58) Field of Classification Search
  CPC ..... B62B 2202/14; A45C 5/146; A61G 7/018; A63B 55/08; B60G 2204/47; B60G 2202/153
  See application file for complete search history.

(56) References Cited

U.S. PATENT DOCUMENTS

| | | | |
|---|---|---|---|
| 4,355,410 A | 10/1982 | Sullins | |
| 4,373,324 A * | 2/1983 | Janos | H02G 11/006 59/78.1 |
| 4,378,191 A * | 3/1983 | Sato | B60P 1/027 254/2 C |
| 4,481,656 A | 11/1984 | Janssen et al. | |
| 4,589,126 A | 5/1986 | Augustsson et al. | |
| 4,619,578 A * | 10/1986 | Routledge | B60G 3/14 180/41 |
| 4,928,283 A | 5/1990 | Gordon | |
| 4,935,949 A | 6/1990 | Fujita et al. | |
| 4,969,167 A | 11/1990 | Zupancic et al. | |
| 4,977,588 A | 12/1990 | Van der Ende | |
| 5,081,662 A | 1/1992 | Warden et al. | |
| 5,146,094 A | 9/1992 | Stark | |
| 5,347,682 A | 9/1994 | Edgerton, Jr. | |
| 5,448,607 A | 9/1995 | McKenna | |
| 5,448,608 A | 9/1995 | Swain et al. | |
| 5,505,482 A * | 4/1996 | VanDenberg | B60G 5/04 280/124.157 |
| 5,638,419 A | 6/1997 | Ingwersen | |
| 5,740,222 A | 4/1998 | Fujita et al. | |
| 5,761,269 A | 6/1998 | Sugihara et al. | |
| 5,956,383 A | 9/1999 | Kendall | |
| 5,982,843 A | 11/1999 | Bailey et al. | |
| 6,065,556 A * | 5/2000 | Andrews | B62D 21/14 180/209 |
| 6,104,775 A | 8/2000 | Tuy | |
| 6,119,034 A | 9/2000 | Herrmann et al. | |
| 6,131,690 A | 10/2000 | Galando et al. | |
| 6,135,700 A | 10/2000 | Collins | |
| 6,176,458 B1 | 1/2001 | Stryke | |
| 6,212,251 B1 | 4/2001 | Tomura et al. | |
| 6,374,937 B1 | 4/2002 | Galando et al. | |
| 6,426,989 B2 | 7/2002 | Grass et al. | |
| 6,456,684 B1 | 9/2002 | Mun et al. | |
| 6,490,333 B1 | 12/2002 | Hsieh | |
| 6,532,623 B1 * | 3/2003 | Watanabe | B60B 33/0057 16/35 D |
| 6,550,101 B2 * | 4/2003 | Plate | B60B 33/04 16/19 |
| 6,609,826 B1 | 8/2003 | Fujii et al. | |
| 6,781,058 B1 * | 8/2004 | DeCicco | B60J 5/06 174/135 |
| 6,789,810 B2 | 9/2004 | Strong | |
| 6,839,937 B2 | 1/2005 | Miller | |
| 6,851,851 B2 | 2/2005 | Smith et al. | |
| 6,909,775 B2 | 6/2005 | Ray et al. | |
| 6,940,941 B2 | 9/2005 | Gregerson et al. | |
| 6,959,068 B1 | 10/2005 | Sommer | |
| 6,963,632 B2 | 11/2005 | Kendall | |
| 6,988,827 B2 | 1/2006 | Mueller | |
| 6,996,204 B2 | 2/2006 | Grass et al. | |
| 7,001,045 B2 | 2/2006 | Gregerson et al. | |
| 7,072,445 B2 | 7/2006 | Kendall | |
| 7,175,347 B2 | 2/2007 | Tybinkowski et al. | |
| 7,215,805 B2 | 5/2007 | Bruder et al. | |
| 7,224,764 B2 | 5/2007 | Sukovic et al. | |
| 7,311,439 B2 | 12/2007 | Muller | |
| 7,338,207 B2 | 3/2008 | Gregerson et al. | |
| 7,388,941 B2 | 6/2008 | Sukovic et al. | |
| 7,394,888 B2 | 7/2008 | Sukovic et al. | |
| 7,397,895 B2 | 7/2008 | Bailey et al. | |
| 7,410,295 B2 | 8/2008 | Distler et al. | |
| 7,438,471 B2 | 10/2008 | Tybinkowski et al. | |
| 7,469,032 B2 * | 12/2008 | Walker | A61B 6/4411 378/38 |
| 7,490,982 B2 | 2/2009 | Gregerson et al. | |
| 7,497,449 B2 | 3/2009 | Logger | |
| 7,568,836 B2 | 8/2009 | Bailey et al. | |
| 7,597,473 B2 | 10/2009 | Graumann et al. | |
| 7,637,660 B2 | 12/2009 | Tybinkowski et al. | |
| 7,956,286 B2 | 6/2011 | Furuichi | |
| 7,963,696 B2 | 6/2011 | Bailey et al. | |
| 8,057,097 B1 | 11/2011 | Tybinkowski et al. | |
| 8,118,488 B2 | 2/2012 | Gregerson | |
| 8,251,584 B2 | 8/2012 | Tybinkowski et al. | |
| 8,303,181 B2 | 11/2012 | Sukovic et al. | |
| 8,403,344 B2 | 3/2013 | Carver et al. | |
| 8,414,219 B2 * | 4/2013 | Lickel | E04F 21/245 404/112 |
| 8,555,578 B2 | 10/2013 | Hushek | |
| 8,636,461 B2 * | 1/2014 | Hammonds | B64F 1/22 414/429 |
| 8,705,695 B2 | 4/2014 | Jabri et al. | |
| 8,737,708 B2 | 5/2014 | Hartmann et al. | |
| 8,746,973 B2 | 6/2014 | Gregerson et al. | |
| 8,753,009 B2 | 6/2014 | Gregerson et al. | |
| 8,770,839 B2 | 7/2014 | Gregerson et al. | |
| 8,888,110 B2 * | 11/2014 | Sadeh | B65D 19/0026 280/43.14 |
| 8,888,364 B2 | 11/2014 | Bailey et al. | |
| 8,905,637 B2 | 12/2014 | Tybinkowski et al. | |
| 9,016,941 B2 | 4/2015 | Tybinkowski et al. | |
| 9,185,301 B2 | 11/2015 | Gregerson et al. | |
| 9,398,886 B2 | 7/2016 | Gregerson et al. | |
| 9,462,984 B2 | 10/2016 | Gregerson et al. | |
| 9,655,572 B2 | 5/2017 | Gregerson et al. | |
| 9,795,022 B2 | 10/2017 | Duhamel | |
| 9,801,592 B2 | 10/2017 | Stanton et al. | |
| 9,820,704 B2 | 11/2017 | Tybinkowski et al. | |
| 10,178,981 B2 | 1/2019 | Bailey et al. | |
| 10,214,168 B1 * | 2/2019 | Yamamoto | B60N 2/90 |
| 2002/0009174 A1 | 1/2002 | Sasaki | |
| 2004/0114723 A1 | 6/2004 | Ray et al. | |
| 2004/0167397 A1 | 8/2004 | Brill et al. | |
| 2004/0170254 A1 | 9/2004 | Gregerson et al. | |
| 2004/0202287 A1 | 10/2004 | Muller | |
| 2004/0228450 A1 | 11/2004 | Mueller | |
| 2005/0117698 A1 | 6/2005 | Lacey et al. | |
| 2005/0135560 A1 | 6/2005 | Dafni et al. | |
| 2007/0092068 A1 | 4/2007 | Albert | |
| 2007/0183588 A1 | 8/2007 | Bailey et al. | |
| 2007/0183589 A1 | 8/2007 | Tybinkowski et al. | |
| 2008/0123818 A1 | 5/2008 | Adler et al. | |
| 2009/0041181 A1 | 2/2009 | Krug | |
| 2009/0185663 A1 | 7/2009 | Gaines, Jr. | |
| 2009/0199674 A1 | 8/2009 | Schena et al. | |
| 2009/0232281 A1 | 9/2009 | Jimbo et al. | |
| 2009/0236157 A1 | 9/2009 | Akamatsu | |
| 2010/0172468 A1 | 7/2010 | Gregerson | |
| 2011/0222667 A1 | 9/2011 | Gregerson et al. | |
| 2012/0104264 A1 | 5/2012 | Bailey et al. | |
| 2014/0259411 A1 | 9/2014 | Sunazuka et al. | |
| 2014/0265182 A1 | 9/2014 | Stanton et al. | |
| 2014/0294159 A1 | 10/2014 | Gregerson et al. | |
| 2016/0128656 A1 | 5/2016 | Gregerson et al. | |
| 2017/0007334 A1 | 1/2017 | Crawford et al. | |
| 2017/0215825 A1 | 8/2017 | Johnson et al. | |
| 2017/0215826 A1 | 8/2017 | Johnson et al. | |
| 2017/0215827 A1 | 8/2017 | Johnson et al. | |

(56) References Cited

U.S. PATENT DOCUMENTS

2018/0014796 A1    1/2018    Stanton et al.
2018/0214098 A1    8/2018    Tybinkowski et al.
2018/0370778 A1*  12/2018  Mathes .................... B62B 3/06

OTHER PUBLICATIONS

International Search Report and Written Opinion from the International Searching Authority for International Patent Application No. PCT/US2011/024585, dated Apr. 4, 2011, 4 pages.
International Preliminary Report on Patentability for International Patent Application No. PCT/US2011/024525, dated Sep. 27, 2012, 11 pages.
International Search Report and the Written Opinion of the International Searching Authority from the Korean Patent Office in International Application No. PCT/US2014/028052 dated Aug. 25, 2014, 14 pages.
International Preliminary Report on Patentability (Chapter 1 of the Patent Cooperation Treaty) for International Application No. PCT/US2014/028052 dated Sep. 24, 2015, 10 pages.
Extended European Search Report received from the European Patent Office in European Application No. 14765786.0-1666 / 2967470 related to PCT/US2014/028052 dated Oct. 10, 2016, 6 pages.
Supplemental European Search Report received from the European Patent Office in European Application No. 14765786.0-1666 /2967470 related to PCT/US2014/028052 dated Oct. 27, 2016, 1 page.
International Search Report for Application No. PCT/US2011/024531 dated Apr. 6, 2011, 2 pages.

* cited by examiner

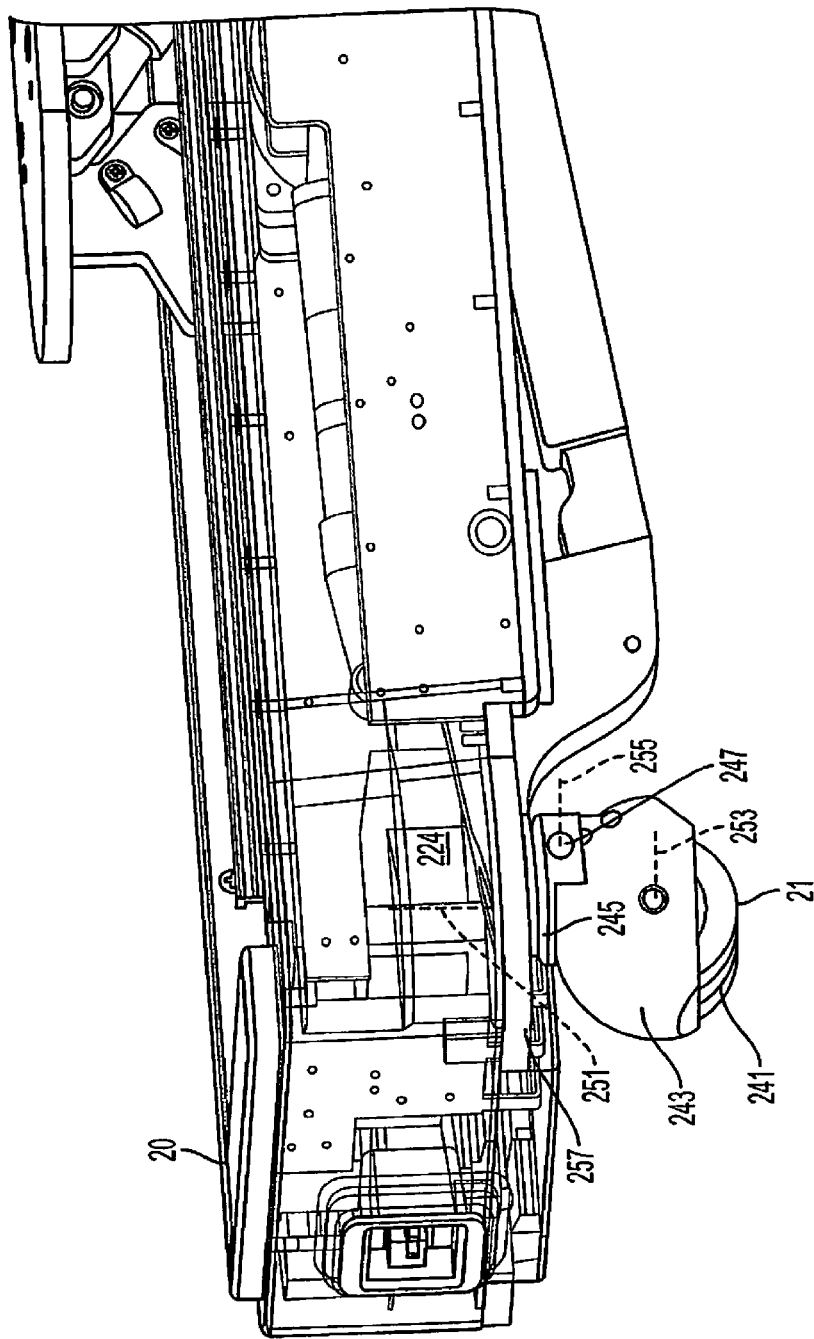

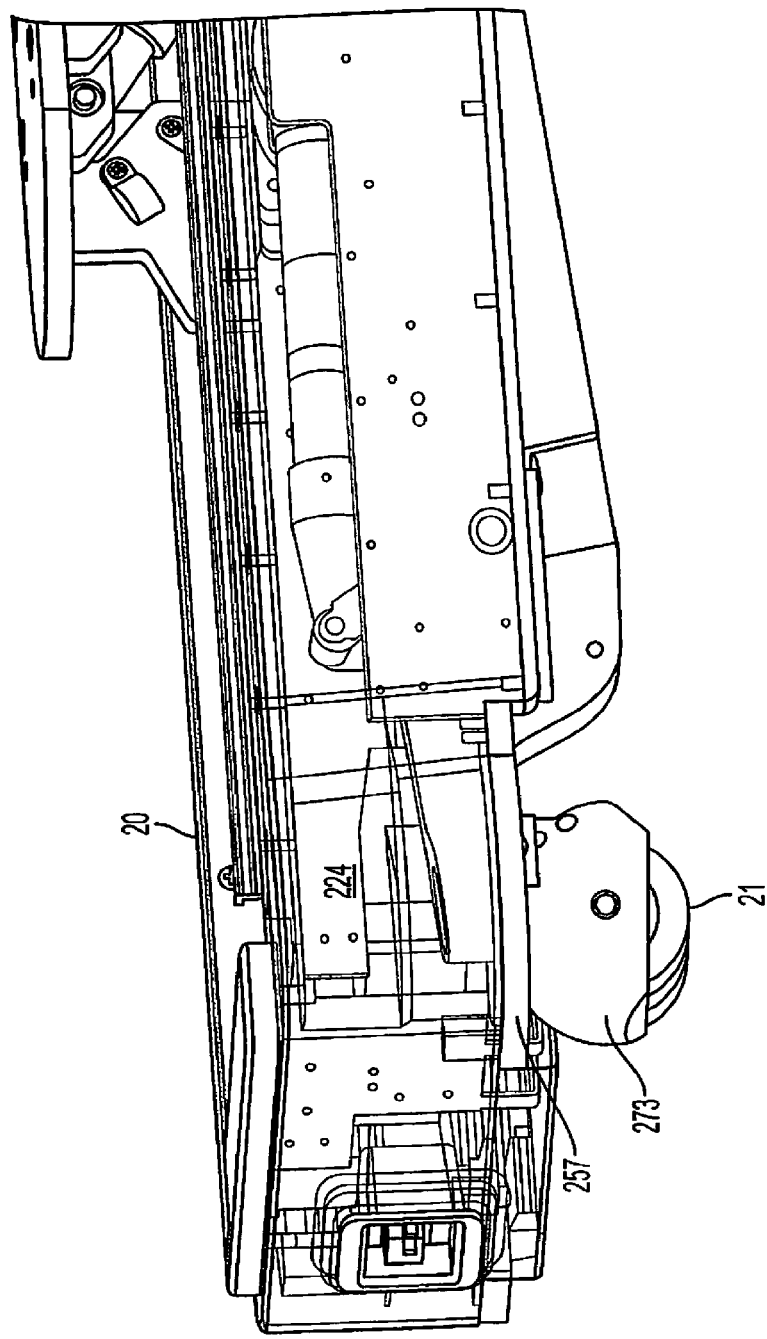

CASTER SYSTEM FOR MOBILE APPARATUS

RELATED APPLICATION

This application claims the benefit of priority to U.S. Provisional Application No. 61/791,509, filed Mar. 15, 2013, the entire contents of which are incorporated herein by reference.

BACKGROUND

Conventional medical imaging devices, such as computed tomography (CT) and magnetic resonance (MR) imaging devices, are typically fixed, immobile devices located in a discrete area reserved for imaging that is often far removed from the point-of-care where the devices could be most useful.

It would be desirable to make these imaging devices mobile, so that they can move to various locations within a hospital or other health services environment. This is difficult due to the size, weight and overall number of components required for making an operable imaging system, and even a relatively small and compact imaging device, such as an x-ray CT scanner, can weigh upwards of 2500 lbs.

There is a need to improve the mobility of imaging systems without sacrificing image quality or adding significantly to the size and weight of the device.

SUMMARY

Various embodiments include a mobile imaging system that includes a base having at least one caster, a first drive mechanism that moves the entire system in a transport mode and translates at least one imaging component relative to the base in a scan mode, and a second drive mechanism that extends the at least one caster relative to the base to raise the base off the ground in the transport mode, and retracts the at least one caster relative to the base to lower the base to the ground in the scan mode.

Further embodiments include a caster system for a mobile apparatus, such as an imaging device, that includes a base containing at least one housing for a caster and at least one caster, attached to the base, the caster having a wheel defining a wheel axis and a swivel joint defining a swivel axis and a pivot point defining a pivot axis, wherein the caster pivots on the pivot axis as the caster is retracted into the housing and extended out of the housing.

Further embodiments include an imaging system that includes a base having a housing, at least one component that translates relative to the base in a scan mode, and a cable management system in the housing and comprising at least one cable that couples at least one of power and data between the base and the at least one component that translates relative to the base, the cable management system having a first end connected to the base and a second end coupled to the at least one component that translates relative to the base and extends in a loop between the first end and the second end such that a leading edge of the loop travels at a lower speed than a speed at which the at least one component translates relative to the base Further embodiments include a method of imaging using a mobile imaging system comprising a base, a first drive mechanism and at least one imaging component mounted to the first drive mechanism, where the method comprises retracting at least one caster relative to the base to lower the base to the ground, translating the at least one imaging component relative to the base to obtain images of an object located above the base, extending the at least one caster relative to the base to raise the base off the ground, transporting the imaging system by driving a drive wheel mechanically coupled to the first drive mechanism when the base is raised off the ground.

BRIEF DESCRIPTION OF THE DRAWINGS

Other features and advantages of the present invention will be apparent from the following detailed description of the invention, taken in conjunction with the accompanying drawings of which:

FIG. 19A illustrates a caster system for mobile apparatus with casters fully extended.

FIG. 19B illustrates the caster system of FIG. 19A with casters partially retracted.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 2:
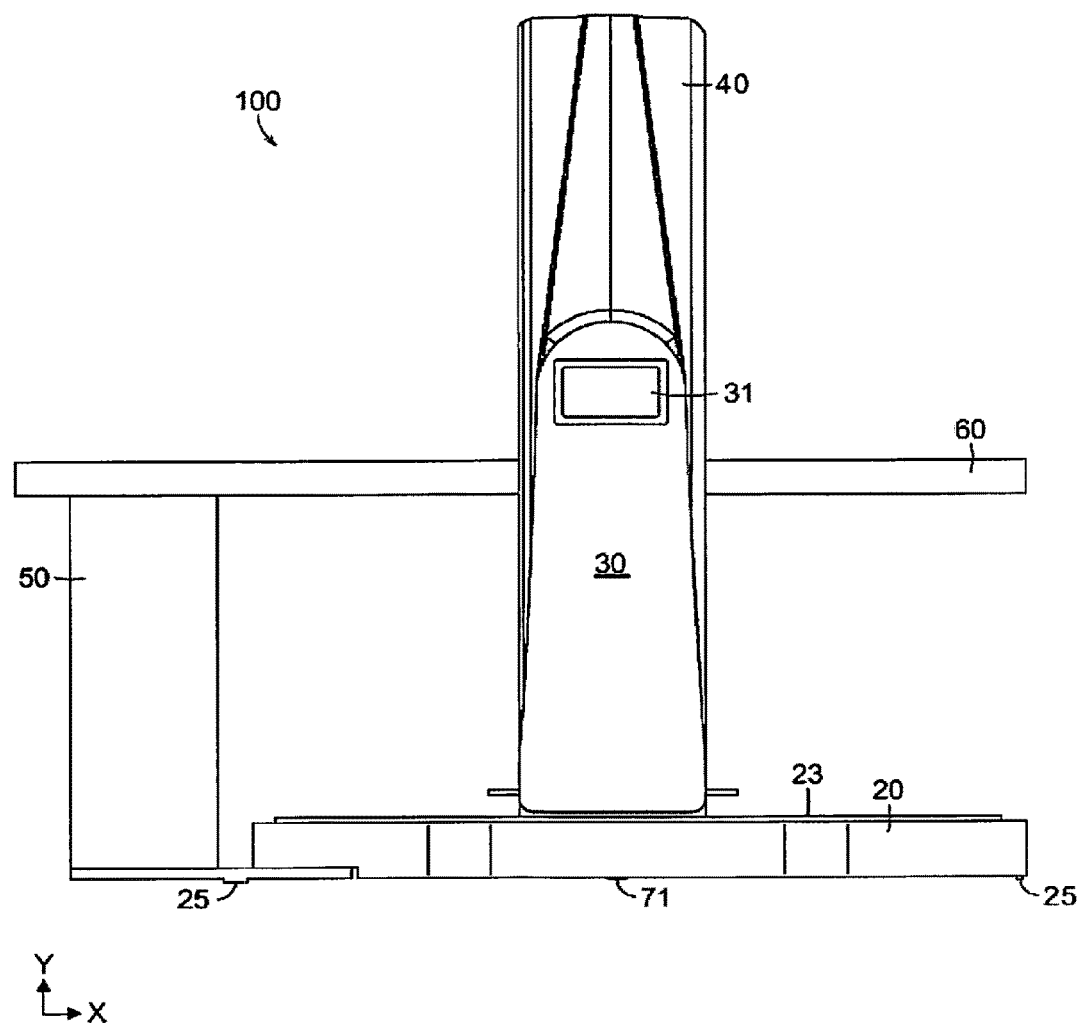
FIG. 2 is a side view of the mobile imaging system with the drive wheel and casters retracted and the base lowered to the floor.
Figure 3:
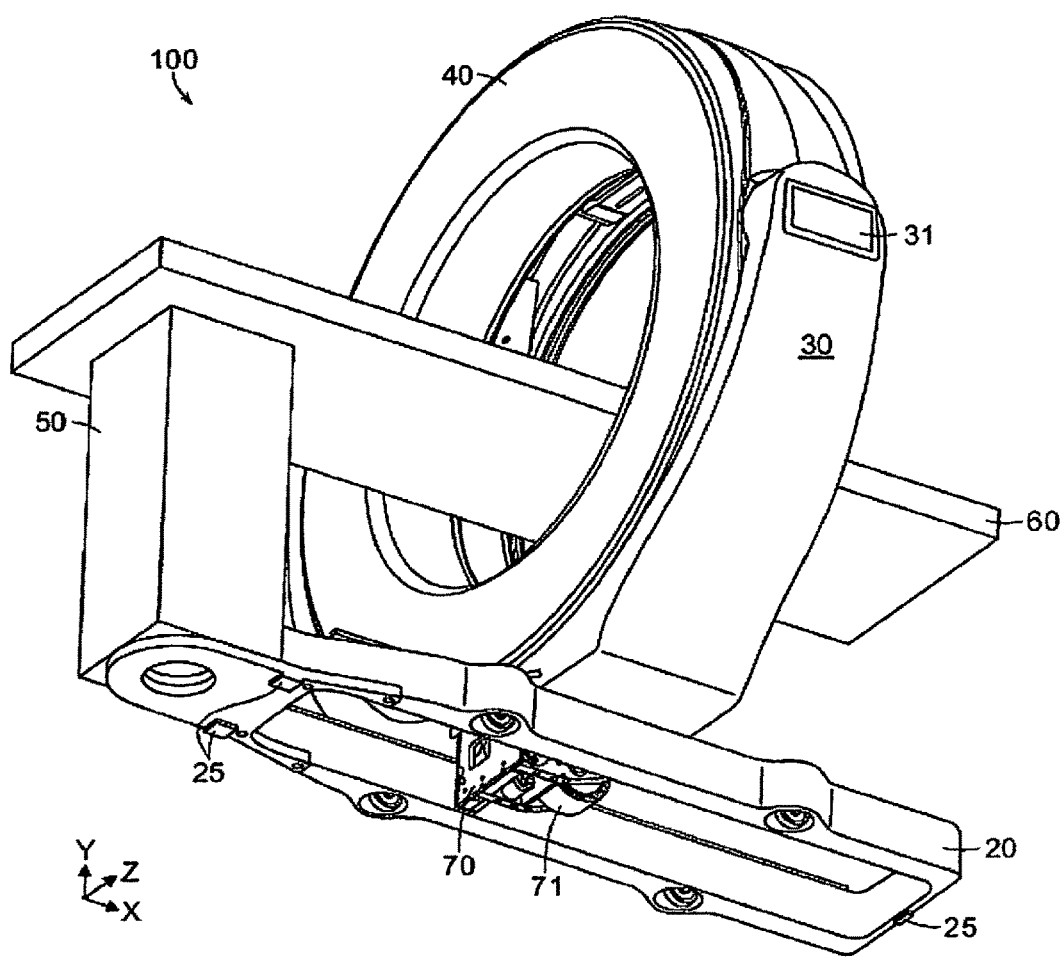
FIG. 3 is a bottom isometric view of the imaging system showing the drive wheel and casters retracted and pads on the bottom surface of the base that define a scan plane.
Figure 4:
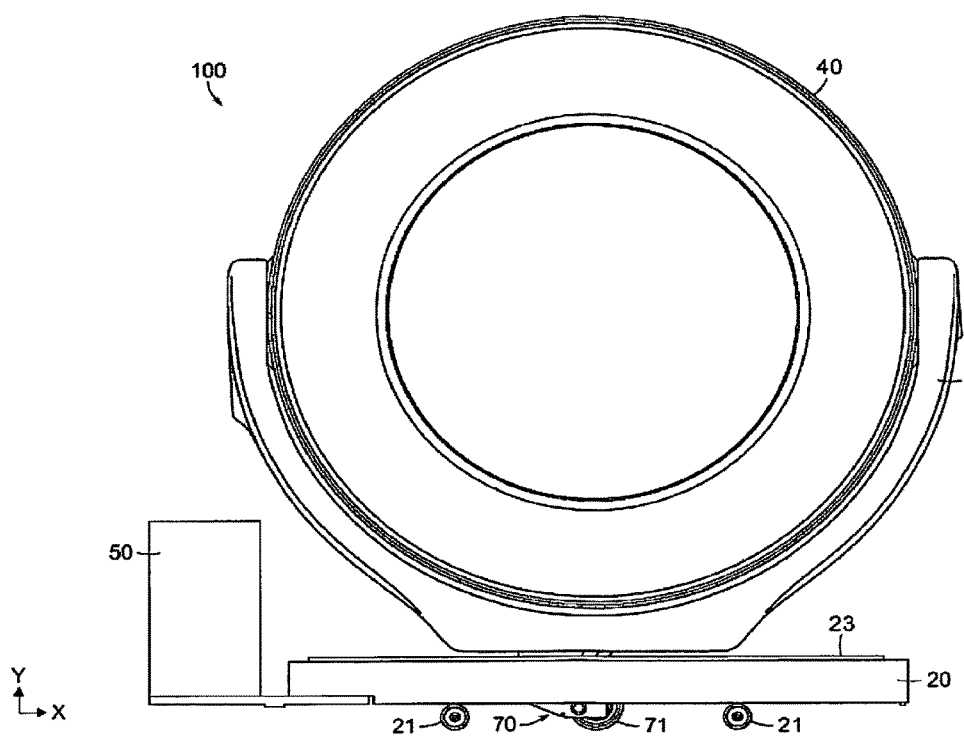
FIG. 4 is a side view of the mobile imaging system in a transport mode.

Referring to FIGS. 1-5, a mobile imaging system 100 according to one embodiment of the invention includes a mobile base 20, a gimbal support 30, a gantry ring 40, and a pedestal 50. The system 100 includes image collection components, such as a rotatable x-ray source and detector array or stationary magnetic resonance imaging components, that are housed within the gantry ring 40. The system 100 is configured to collect imaging data, such as, for example x-ray computed tomography (CT) or magnetic resonance imaging (MRI) data, from an object located within the bore of the gantry ring 40, in any manner known in the medical imaging field. As shown in FIGS. 1-3 and 5, the pedestal 50 is adapted to support a tabletop support 60 that can be attached to the pedestal 50 in a cantilevered manner and extend out into the bore of the gantry ring 40 to support a patient or other object being imaged. As shown in FIG. 4, the tabletop support 60 can be partially or entirely removed from the pedestal 50, and the gantry ring 40 can be rotated relative to the base 20, preferably at least about 90 degrees, from an imaging position (FIGS. 1-3 and 5) to a transport position (FIG. 4) to facilitate transport and/or storage of the imaging system.

Figure 5:
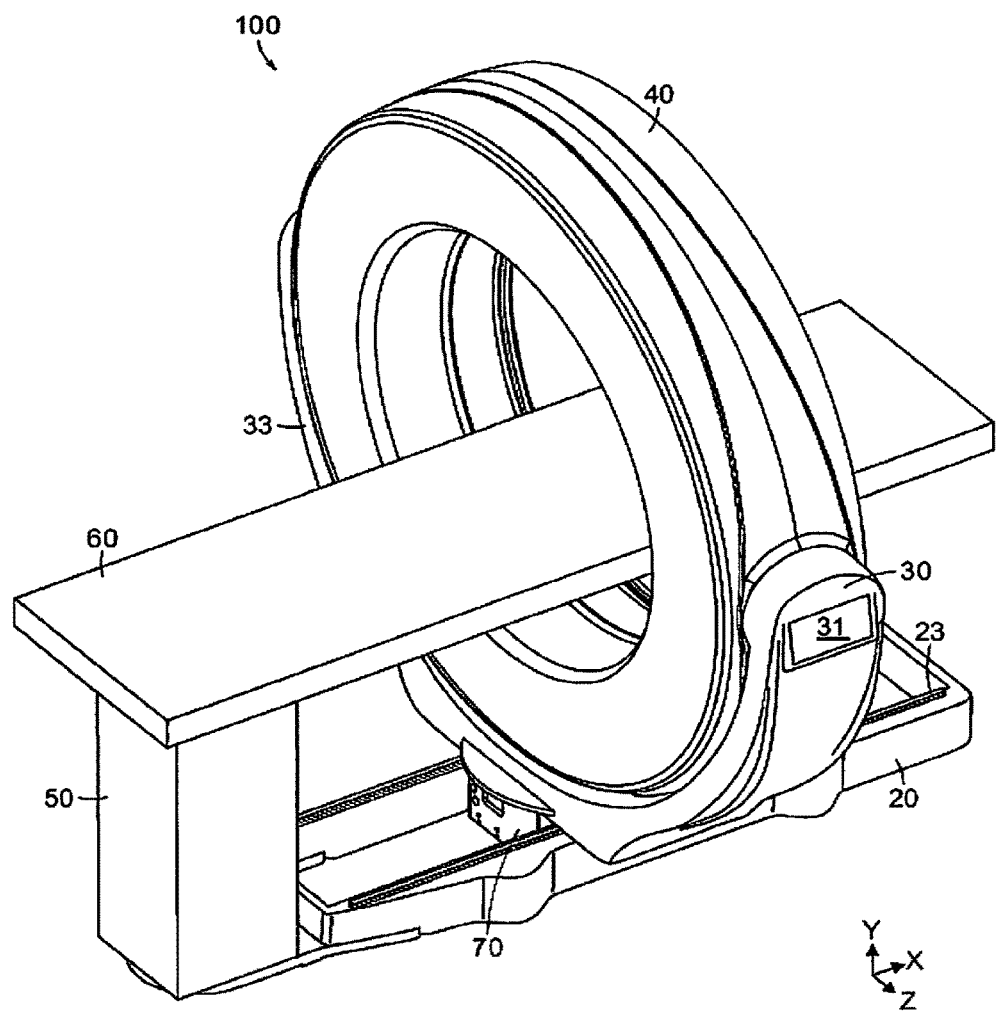
FIG. 5 is an isometric view of the mobile imaging system in a scan mode.
Figure 6:
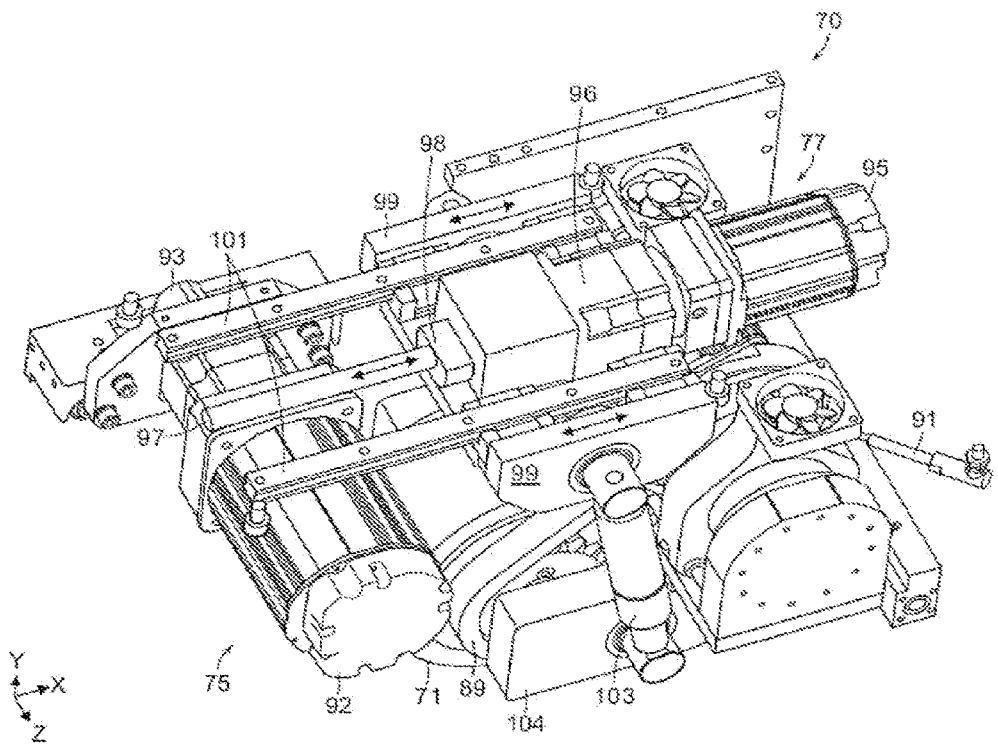
FIG. 6 is a top isometric view of the drive mechanism for an imaging system according to one embodiment.

As illustrated most clearly in FIGS. 3 and 5, the system 100 includes a drive mechanism 70. The drive mechanism 70 is mounted beneath the gimbal 30 and the gantry ring 40 and within the base 20. The drive mechanism 70 also comprises a drive wheel 71 that can extend and retract between a first extended position (FIG. 1) to facilitate transport of the imaging system 100, and a second retracted position (FIGS. 2 and 3) during an image acquisition procedure (e.g., scan). The drive mechanism 70 includes a main drive (described in further detail below) that is geared into the drive wheel 71 when the drive wheel 71 is in the first extended position (FIGS. 1 and 3) to propel the imaging system 100 across a floor or other surface, and thus facilitate transport and positioning of the system 100. According to one aspect, the drive wheel 71 is decoupled from the main drive when the drive wheel 71 is in the second retracted position (FIGS. 2 and 3), thus preventing the system 100 from back driving the main drive gearbox and motor during an imaging procedure.

Figure 1:
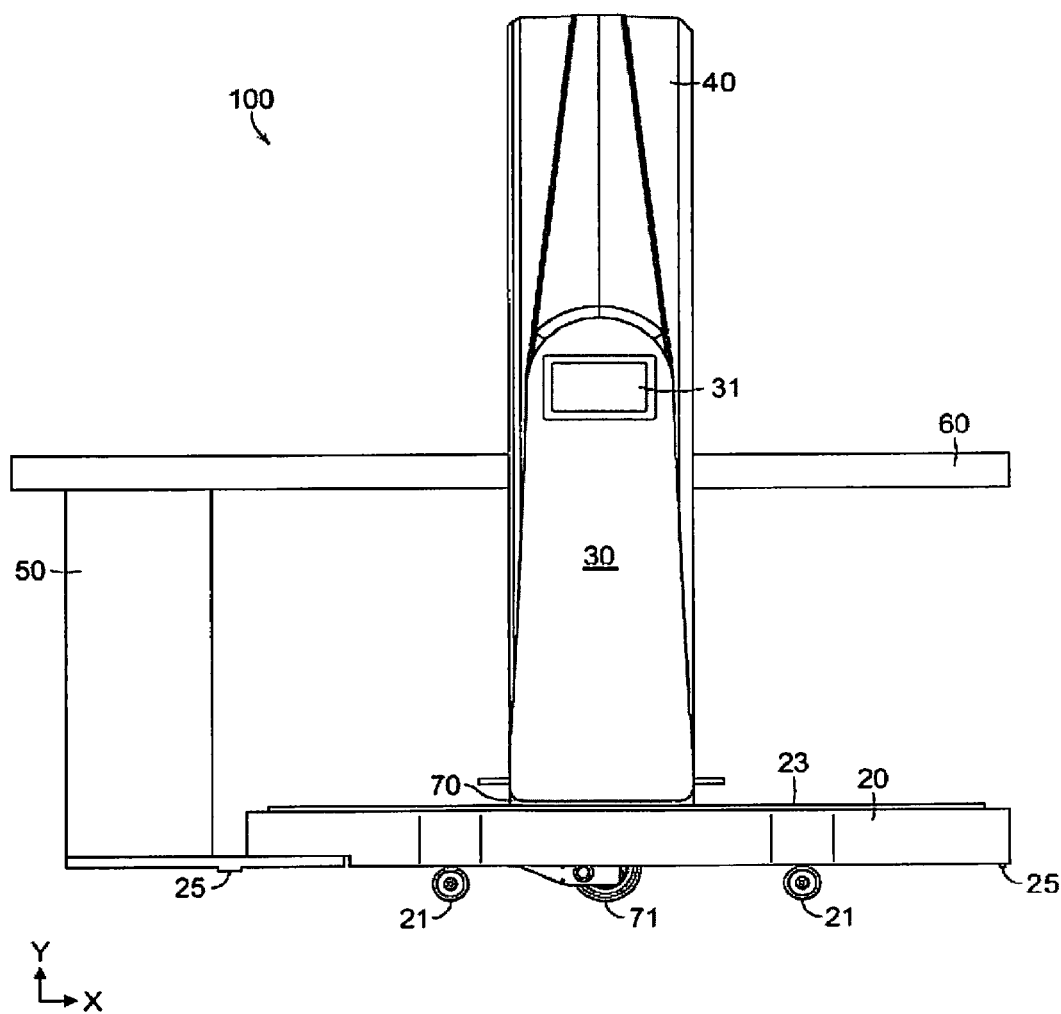
FIG. 1 is a side view of a mobile imaging system with a drive wheel and casters extended and the base of the system raised off the floor.

As is illustrated in FIGS. 3 and 5, the base 20 is a sturdy, generally rectilinear support structure. The base 20 includes a central opening extending lengthwise along the base, and the drive mechanism 70 is positioned inside the central opening. As seen in FIG. 3, the bottom of the base 20 includes a plurality of pockets that contain retractable casters 21. The casters 21 can be spring-loaded and biased to extend from the bottom of the base 20 when the system is raised off the ground, as shown in FIGS. 1 and 4. When the drive wheel 71 is retracted and the system 100 is lowered to the ground, as shown in FIG. 2, the casters 21 are retracted into their respective pockets. In an alternative embodiment, an active drive system, rather than a passive spring-based system, can drive the extension and retraction of the casters in their respective pockets.

The top of the base 20 is shown in FIG. 5, and includes a pair of parallel rails 23 running lengthwise on the top surface of the base, on either side of the central opening of the base. During an imaging scan, the gantry 40, gimbal 30 and drive mechanism 70 translate along an imaging axis relative to the base 20, pedestal 50 and patient support 60. Bearing surfaces, which can be located on or attached to the drive mechanism 50 and/or gimbal 30, mate with the rails 23 to guide the translation motion relative to the base. The drive mechanism 70 can include a scan drive (described in further detail below) that drives the translation motion of the drive mechanism 70, gimbal 30 and gantry 40 relative to the base 20.

The base 20 can be made compact and relatively lightweight to improve the portability and usability of the system 100. Minimizing the height and width of the base 20 minimizes interference with the operator's feet as the operator approaches a patient on the support table. A further advantage of this embodiment is that the wheels, including drive wheel 71 and casters 21, retract within the base during imaging, and thus cannot interfere with the operator. The drive mechanism 70 in this embodiment is small and compact, and is generally hidden beneath the gimbal 30 and gantry ring 40 and positioned inside the central opening of the base 20, and advantageously does not interfere with the operator or with the loading/unloading of a patient or patient support table. Positioning the wheels within the base also minimizes the risk of injury (e.g., running over a person's foot) during transport of the system. It will be further noted that in this embodiment, the width of the base 20 tapers at the end of the base supporting the pedestal 50. An advantage of this design is that it allows a cart or shuttle to more easily approach the pedestal-end of the system 100 in order to transfer a patient support table 60 to the top of the pedestal 50 for imaging, or to remove the support table 60 from the top of the pedestal 50 following imaging. The shape and size of the base 20 and pedestal 50 can be designed to mate with the cart to facilitate the interchange of patient support tables. Suitable patient support tables and transport carts are known in the art, and examples are described in the JUPITER system brochure (11/2008) from TRUMPF Medezin Systeme GmbH & Co. KG of Puchheim, Germany, the entire contents of which are incorporated herein by reference.

In one embodiment, the width of the base 20 is approximately equal to or less than the width of the patient support table. At its widest (e.g., from the outside of the caster pockets), the base 20 can be less than about 25 inches wide, and can be around 22 or 23 inches wide. The central opening of the base can be about 13 inches across, or any other suitable dimension to accommodate the drive mechanism 70. The base 20 is generally less than about 6 inches in height when the system is lowered on the floor. The drive mechanism 70 is preferably very compact to maximize the translation motion of the gantry ring 40 relative to the base 20 and the support table 60. In one embodiment, the gantry ring 40 can translate at least about 40 inches to 48 inches.

Conceptually, the imaging system 100 according to this embodiment can be considered to include two separate sub-assemblies. The first sub-assembly is comprised of the base 20, pedestal 50 and patient table 60. The second sub-assembly includes the drive mechanism 70, the gimbal 30 and the gantry ring 40. This second sub-assembly includes most or all of the imaging components on the gantry ring 40, and is generally much heavier than the first sub-assembly. By way of example, for an x-ray CT scanning system, the gimbal and gantry sub-assembly can weigh on the order of 1400 to 1500 lbs., whereas the base/pedestal/table sub-assembly typically only weighs about 1000 lbs. or less.

According to one aspect, the drive mechanism 70 supports the weights of the gimbal 30 and gantry ring 40 during imaging procedures as well as during transport of the system. The base 20 and pedestal 50 are supported on the casters 21 during transport of the system. During imaging, the base 20 is lowered and can be supported on the ground. The drive mechanism 70 is configured such that even when the drive wheel 71 is retracted (FIGS. 2 and 3), the wheel 71 still contacts the ground and supports the weight of the gantry and gimbal sub-assembly. The drive mechanism supports at least a portion of the weight of the gantry and gimbal sub-assembly—i.e. greater than 0% and up to 100% of the weight of these components. In one embodiment, at least 50% of the weight of gantry and gimbal is supported by drive mechanism 71. In other embodiments, at least 60%, at least 70%, at least 80%, at least 90% and more than 95% of the weight of the gimbal and gantry sub-assembly is supported by the drive mechanism 71.

With this arrangement, the comparatively heavier weight of the gimbal/gantry sub-assembly does not need to be supported by the base of the system, which means the base can be made smaller and lighter for improved portability. Further, since the imaging gantry is supported at all times at least in part by the drive mechanism, the gantry can translate a relatively long distance along the length of the base while minimizing the possibility of beam deflection, which can result in variations of the scan plane and negatively effect image reconstruction. As shown in FIG. 3, the bottom surface of the base 20 includes at least three pads 25 that define a single imaging plane. When the base 20 is lowered to the floor, the base 20 rests on the pads 25, which define a single reference plane for the base, pedestal and table assembly, which are fixed relative to the pads 25. The pads 25 maintain this reference plane even when there are elevation differences in the floor. The rails 23 of the base, upon which the gimbal and gantry translate, are similarly fixed in relation to the pads 25, and define an imaging plane, parallel to the reference plane, for the imaging components of the gantry. According to one aspect, the drive mechanism 70 includes a suspension system (described further below) between the drive wheel 71 and the gantry that supports the weight of the gimbal and gantry and allows the drive wheel to conform to elevation differences in the floor while the gimbal and gantry translate in the imaging plane defined by the rails, further minimizing deflection of the imaging plane path of the imaging components.

During transport mode, the drive mechanism 70 extends the drive wheel 71 downward as shown in FIGS. 1 and 4, which causes the base 20 to raise off the ground and the casters 21 to extend. As previously noted, the casters 21 can be spring-loaded to extend when the base 20 is lifted off the ground, or alternatively, they can be actively extended by a suitable drive apparatus. The drive mechanism 70 can include a suspension system (described in further detail below) to drive the extension and retraction of the drive wheel 71. During transport mode, the drive mechanism 71, along with the gimbal 30 and gantry ring 40, can translate to the approximate center of the base 20, as shown in FIG. 4, so that these heavier components are approximately centered between the casters 21. This helps improve the balance and stability of the system during transport. The gimbal 30 and gantry ring 40 can be rotated into transport position, as shown in FIG. 4. A pin system can lock the drive mechanism 70, gimbal 30 and gantry ring 40 in place relative to the base 20 so that the entire system can be easily transported. The drive mechanism's main drive, which drives the drive wheel 71, can be servo-controlled, and the system 100 can be driven, in both forward and reverse directions, in response to a user input command. The suspension system of the drive mechanism 71 can be an active suspension system, as described below, which can aid in driving the imaging system 100 over uneven surfaces, such as thresholds and ramps. Steering of the system can be achieved by pivoting the system 100 around the centrally-located drive wheel 71, using the casters 21 for balance and support. A handle or other steering mechanism can be provided on the system (such as on the gimbal, gantry, or pedestal) to assist in driving the system. A strain gauge, throttle, button or other user-input mechanism located on the system can provide servo-feedback down to the drive mechanism to control the driving of the drive wheel 71. In one embodiment, shown in FIGS. 1-3 and 5, the system 100 can include a display system 31 that includes a camera on one side of the system and a display screen, such as an LCD display, on the opposite side of the system that allows the operator positioned behind the system to see obstacles in front of the system, which further assists the transport of the system. The system 100 can include a collision detection system, such as an audio or visual range-finder device, to further assist in transporting the device.

Turning now to FIGS. 6-16, a drive mechanism 70 in accordance with one embodiment of the invention is shown. The drive mechanism 70 can include three drive systems: a main drive assembly 73 that is coupled to and drives the drive wheel 71 for transporting the imaging system, a scan drive assembly 75 for translating the imaging components relative to the system base during an imaging scan, and a suspension drive assembly 77 that controls the extension and retraction of the drive wheel 71.

The main drive 73 is shown most clearly in FIGS. 7, 11A, 11B, and 16, and includes a motor 81, a sprocket 83 that can be connected by a drive chain 89 (FIG. 6) to the drive wheel 71, a gearbox 82, a sliding yoke 84, and a brake mechanism 86. As noted above, the main drive 73 is engaged to the drive wheel 71 when the wheel is extended in transport mode, and is de-coupled from the drive wheel when the wheel is retracted during an imaging mode. The engagement and disengagement of the drive wheel 71 is accomplished by the sliding yoke 84, which is connected to a main drive decoupling linkage 91 (FIGS. 12B and 13). As the drive wheel 71 retracts and extends, the decoupling linkage 91, which can be a rotating piston and sleeve assembly, causes the yoke 84 to reciprocate, as shown by the arrow in FIG. 7. This causes a sliding spline 85 (FIG. 16), connected to the yoke 84, to move in and out of mating engagement with the sprocket 83, thereby controlling the engagement and disengagement of the drive wheel 71 from the motor 81 and gearbox 82. The yoke 84 and spline 85 can be spring-biased into a disengaged position, and only when the drive wheel is in an extended position does the wheel 71 become engaged to the main drive.

Figure 7:
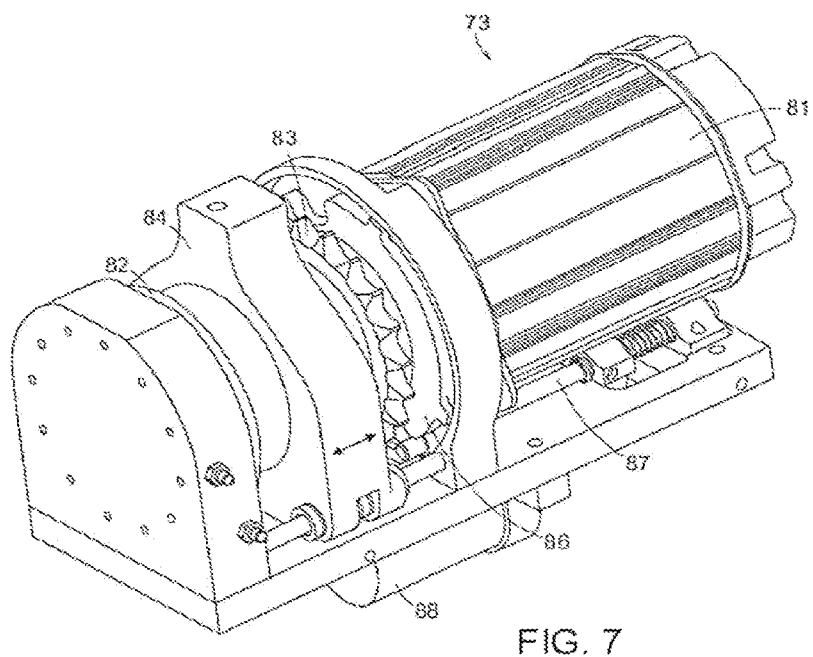
FIG. 7 is an isometric view of the main drive assembly.

The main drive 73 also includes a brake mechanism, which includes a rotating brake disc 86, a spring-loaded brake rod 87, and a brake solenoid 88. The brake disc 86 can be coupled to the sprocket 83. The brake rod 87 can be biased to extend beyond the brake disc 86, as shown in FIG. 7, which prevents the sprocket 83 and drive wheel 71 from rotating. The brake mechanism thus functions similar to a parking brake in an automobile. When the solenoid 88 is energized, it drives the brake rod 87 to retract away from the brake disc 86, which is then free to rotate along with the sprocket 83 and drive wheel 71. An important safety feature of this design is that if the imaging system 100 loses power, the brake rod automatically extends to stop the motion of the drive wheel 71.

The scan drive assembly 75 is shown in FIGS. 6, 8-10 and 12A-13. The scan drive assembly 75 drives the translation of the drive mechanism 70, gimbal 30 and gantry ring 40 relative to the base 20. In this embodiment, the scan drive assembly 75 is mounted adjacent the main drive assembly 73 and drive wheel 71. All of these components are mounted beneath the gimbal 30 and gantry ring 40 in a compact space, generally in the opening within the base 20. The scan drive assembly 75 in this embodiment includes a motor 92 and a belt drive 93, which is shown most clearly in FIGS. 8 and 10.

Figure 8:
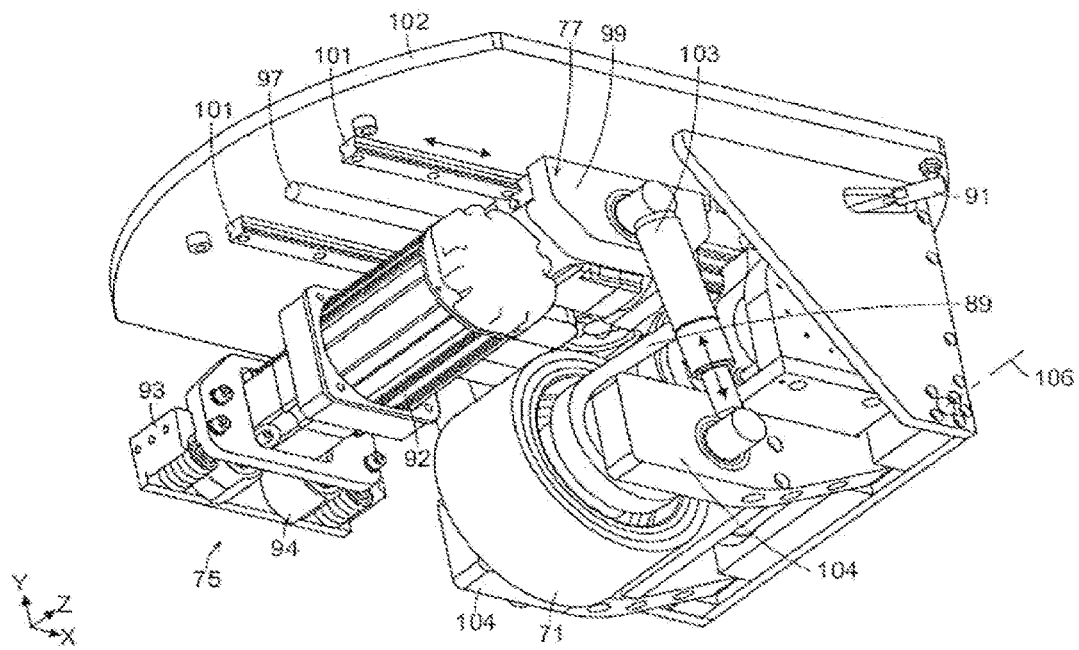
FIG. 8 is a bottom isometric view of the drive mechanism.
Figure 9:
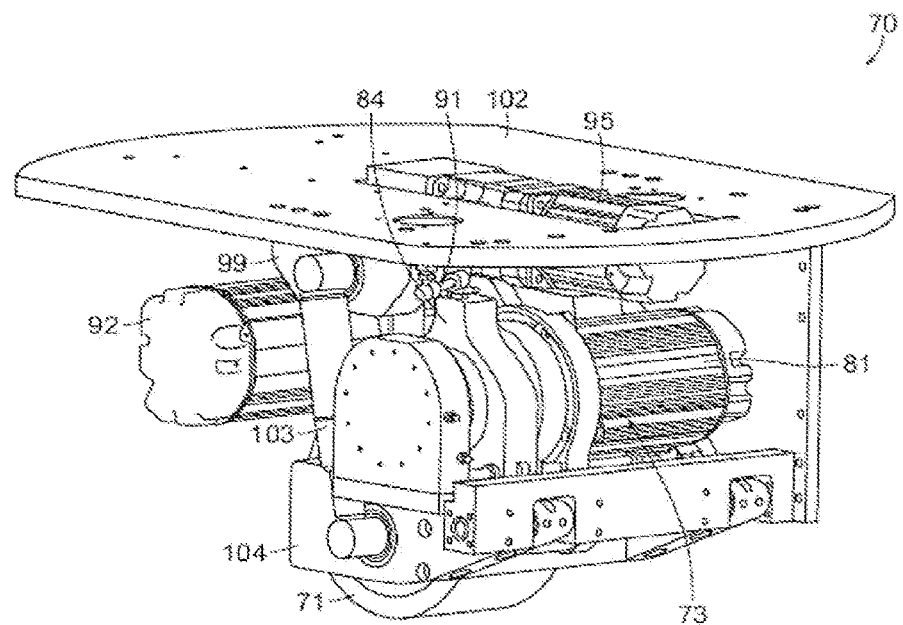
FIG. 9 is a rear isometric view of the drive mechanism.
Figure 10:
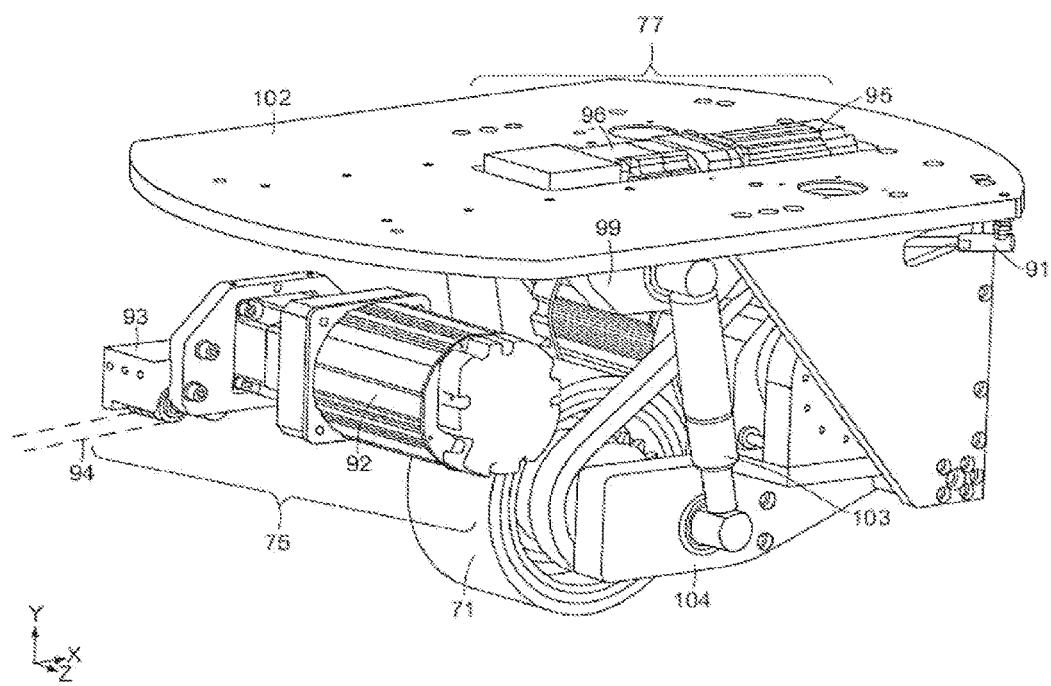
FIG. 10 is a front isometric view of the drive mechanism.
Figure 11A:
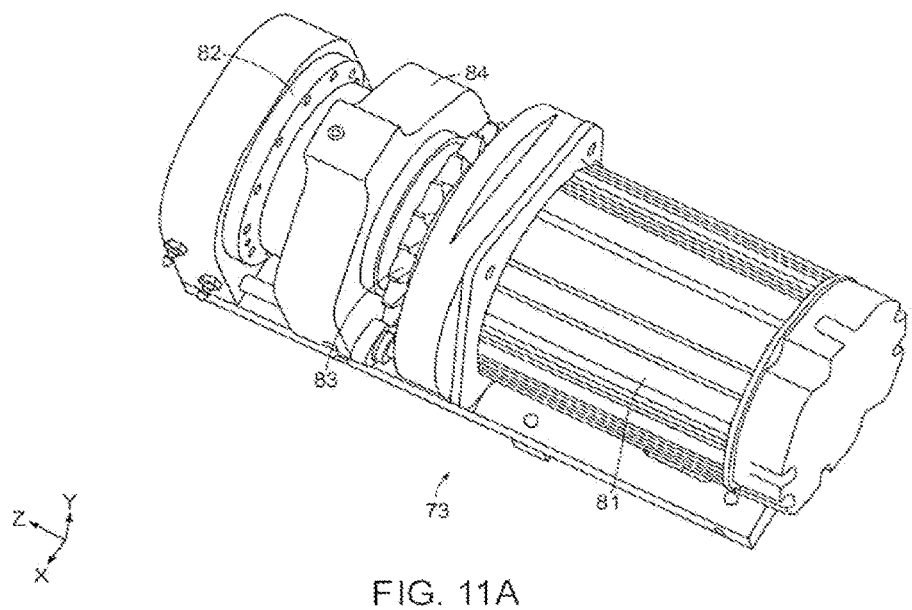
FIGS. 11A and 11B are top isometric views of the main drive assembly.
Figure 11B:
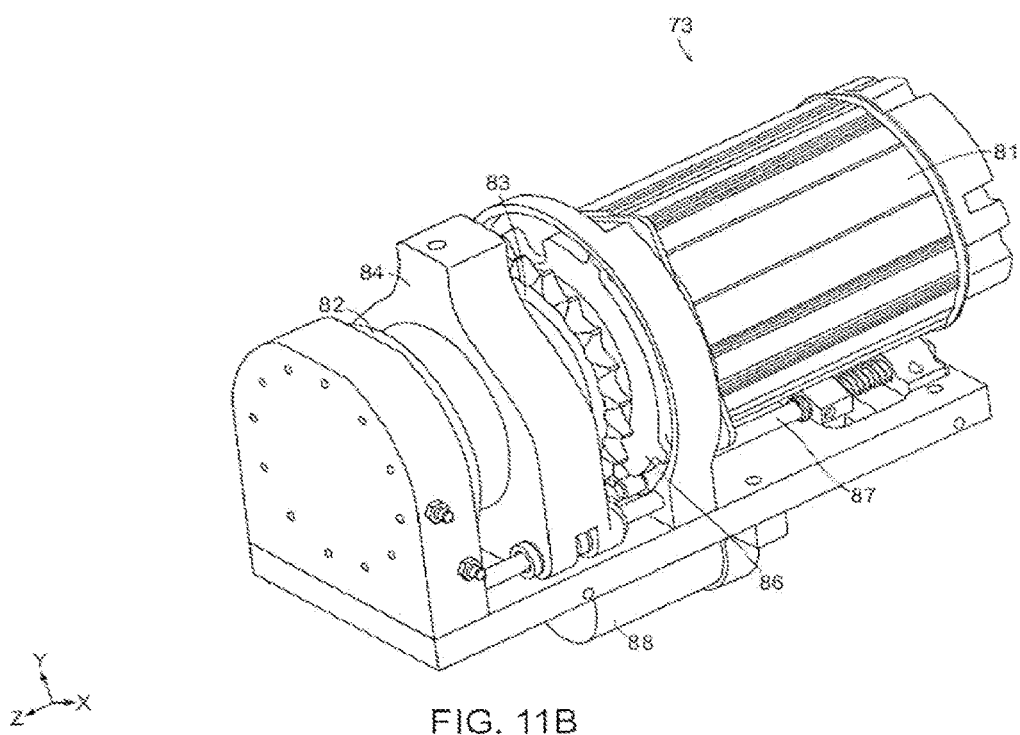

The belt drive 93 mates with a bearing surface on the base 20 in order to effect the translation of the drive mechanism, gimbal and gantry ring relative to the base. In one embodiment, the belt drive 93 mates with a bearing surface, which can be a lip or rail (not shown), provided on an interior wall of the central opening of the base 20 (FIGS. 3 and 5). A belt 94 is secured to the bearing surface and is looped through the belt drive 93, where it meshes with a pulley driven by the scan drive motor 92, as shown in FIGS. 8 and 10. The rotation of the scan drive motor 92 thus causes the scan drive assembly 75 to traverse along the length of the belt 94, and thereby translate the gantry, gimbal and drive mechanism relative to the base. The belt drive 93 can be servo-controlled, with a linear encoder device, and have substantially zero or minimal backlash, to provide precise, controlled fine-scanning of the imaging components relative to the base and patient support table. Any suitable configuration for achieving translation using a scan drive disposed within the drive mechanism can be employed.

The suspension drive assembly 77 is shown most clearly in FIGS. 6, 8-10, and 12A-15. The suspension drive assembly comprises a motor 95 and gearbox 96 that drive the rotation of a lead screw 97. A lead screw nut 98 translates with the rotation of the lead screw 97, as indicated by the "nut travel" arrow shown in FIG. 6. The lead screw nut 98 is mechanically coupled to a pair of rail carriages 99, so that the translation of the lead screw nut 98 causes the rail carriages 99 to translate on a pair of rails 101 that are fixed to the upper plate 102 of the drive mechanism 70, as shown in FIG. 8. The rail carriages 99 are each connected to one end of a spring 103, which can be a gas spring, as shown in FIG. 8. The other end of each spring 103 is connected a respective swing arm 104 that can pivot with respect to the drive mechanism around an pivot axis 106. As can be seen in FIG. 8, for example, the translation of the rail carriages 99 causes the springs 103 to articulate with respect to the rail carriages 99 and the swing arms 104, which in turn causes the swing arms 104 to pivot, as shown generally by the arrow in FIG. 8. The drive wheel 71 is mounted between the two pivoting swing arms 104, so that the translation of the rail carriages 99 and the resulting pivoting motion of the swing arms 104 causes the drive wheel 71 to extend and retract relative to the upper plate 102 of the drive mechanism 70.

Figure 12A:
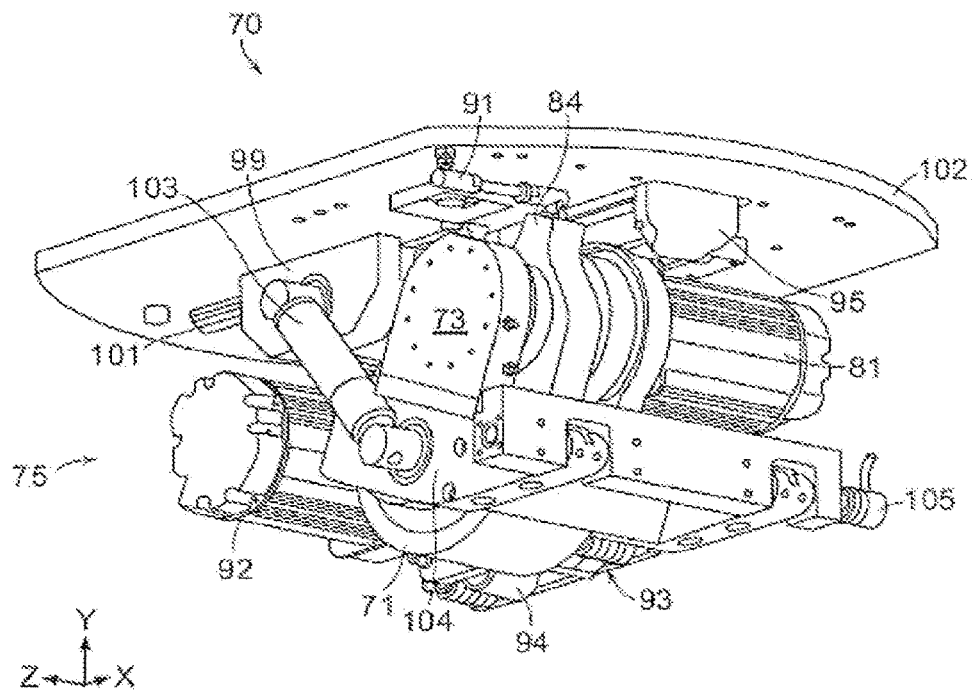
FIGS. 12A and 12B are bottom isometric views of the drive mechanism.
Figure 12B:
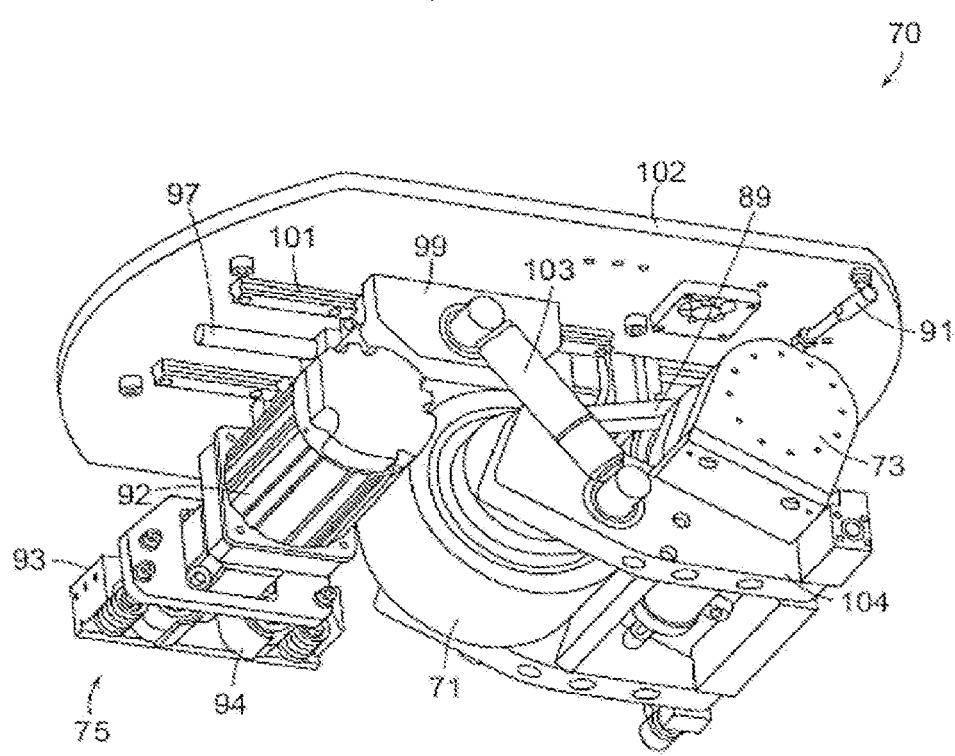
Figure 13:
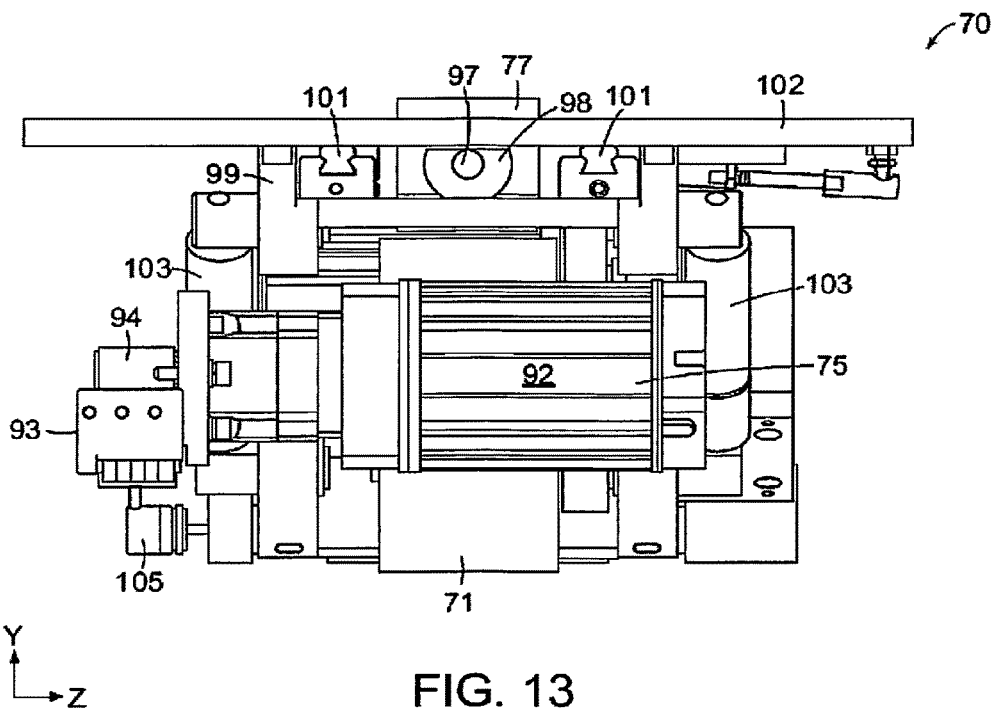
FIG. 13 is a front view of the drive mechanism.
Figure 14:
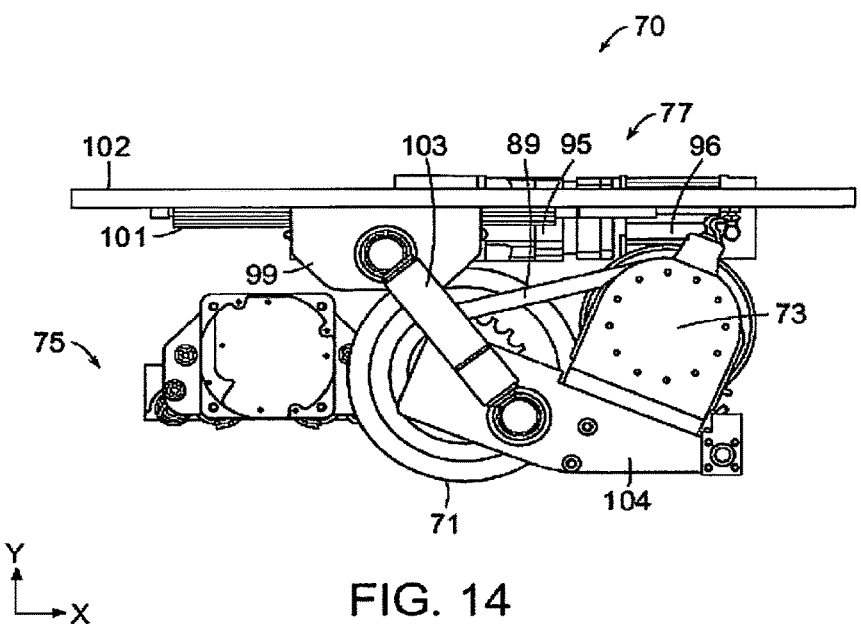
FIG. 14 is a side view of the drive mechanism.
Figure 15:
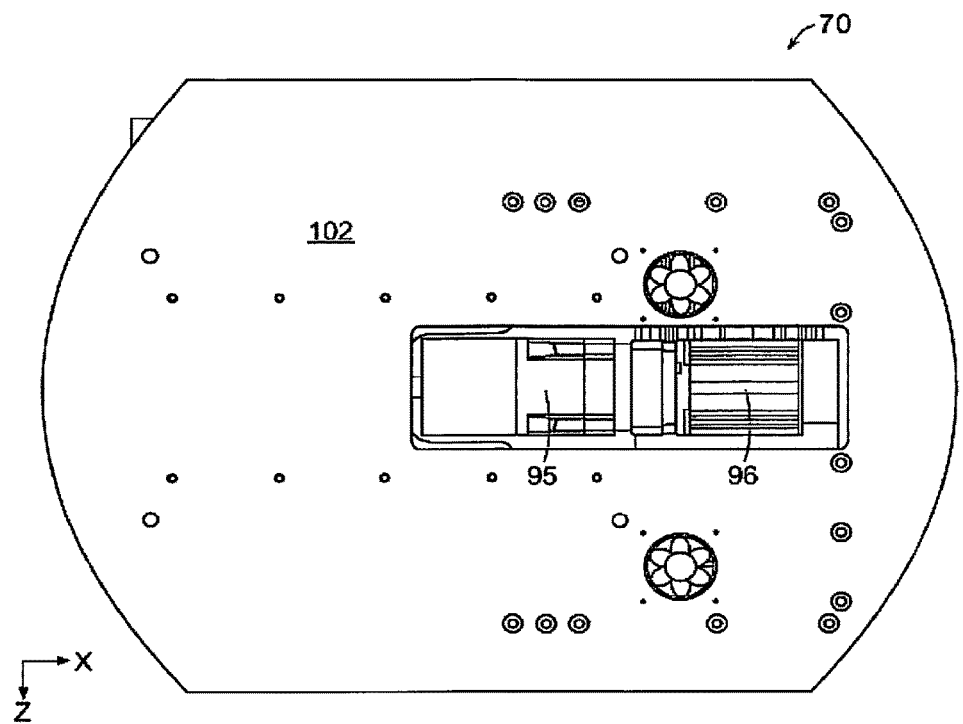
FIG. 15 is a top view of the drive mechanism.
Figure 16:
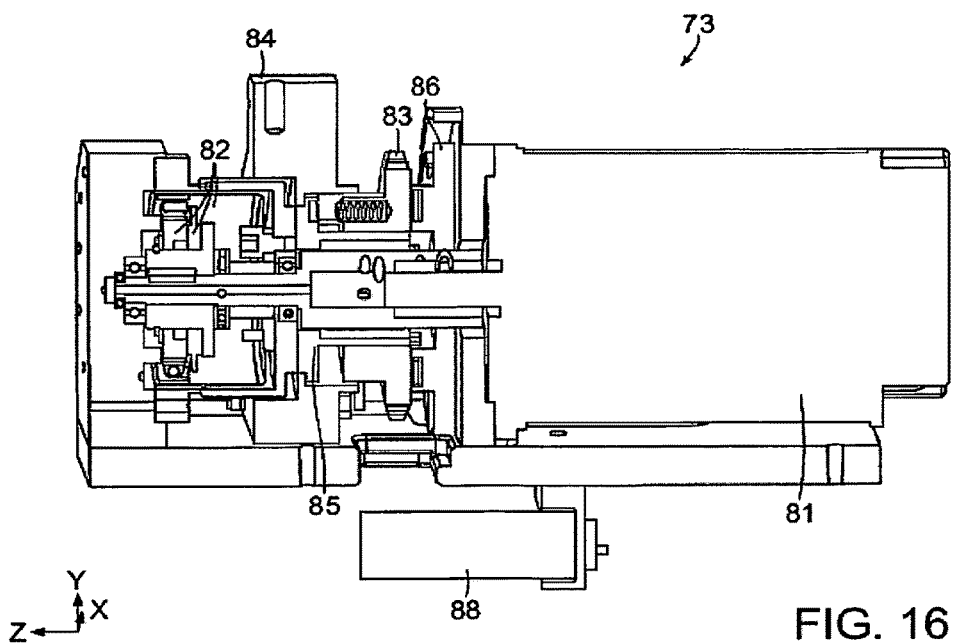
FIG. 16 is a cross-sectional view of the main drive assembly.

As can be seen in FIGS. 12A and 12B, the main drive 73 can be mounted to the swing arms 104. In this way, as the rail carriages 99 translate causing the swing arms 104 to pivot, the main drive engagement/disengagement linkage 91, which connects the upper plate 102 of the drive mechanism 71 to the sliding yoke 84 of the main drive 73, acts on the sliding yoke 84 to selectively engage and disengage the main drive 73 to and from the drive wheel 71. As previously discussed, in one embodiment, the drive wheel 71 is engaged to the main drive 73 only when it is in an extended position—i.e., when the swing arms 104, main drive 73 and drive wheel 71 are pivoted down and away from the upper plate 102 of the drive mechanism 70. When the drive wheel 71 is retracted—i.e., the swing arms 104, main drive 73 and drive wheel 71 are pivoted upwards towards the upper plate 102, the yoke 84 slides back to disengage the main drive 73 from the drive wheel 71.

It will be noted that when the drive wheel 71 is retracted, the base 20 automatically lowers to the ground and rests on pads 25, as shown in FIGS. 2, 3 and 5. During an imaging scan, the weight of the gimbal 40 and gantry 30 remains supported by the drive wheel 71, which is able to freely-rotate as the gimbal and gantry translate on the rails 23 of the base. One advantage of this configuration is that the heavy gimbal and gantry ring assembly can be easily moved manually relative to the base, such as may be required in order to quickly access a patient during an emergency situation.

The springs 103 function as a suspension system between the drive wheel 71 and the gimbal 30 and gantry ring 40, which are supported by the drive wheel 71 during both transport and imaging modes. The springs 103 can contract to allow the wheel 71 to conform to elevation differences in the floor during an imaging scan, while the drive mechanism 70, gimbal 30 and gantry ring 40 translate on the base 20 during an imaging scan. This can greatly reduce or eliminate deflection of the scan plane path of the imaging components during the fine movement scan. During transport of the system 100, the springs 103 can facilitate transport of the system over uneven surfaces, including door thresholds and ramps, for example. In one embodiment, the suspension system is an active suspension system that can maintain a controlled force between the drive wheel and the floor. In this embodiment, the springs 103 and suspension drive assembly 77 can include an active servo-control system that can continually adjust the translation of the rail carriages to maintain a substantially constant spring displacement, and thus maintain a substantially constant force between the wheel and the floor. As shown in FIGS. 12A and 13, for example, an encoder 105 can be provided on at least one of the swing arms 104 to measure the displacement of the swing arm 104 and spring(s) 103 relative to the upper plate 102. The encoder 105 can provide a feedback signal to the suspension drive 77 to make continual fine adjustments and control the force between the wheel and the floor.

The drive wheel 71 can comprise a suitable elastomeric material that is rated to safely support the weight of the imaging components in the gimbal and gantry ring assembly. For example, the wheel can be rated to support about 1900 lbs. A softer durometer material for the wheel will provide better grip and minimize the risk of slippage, but may not be rated to support the required weights.

An advantage of the present drive mechanism 71 is that it is easily accessible for servicing and repair. For example, the drive wheel can be extended to raise the system off the floor and provide easy access to any components of the drive mechanism 71. If the drive mechanism 71 needs to be removed, the system can be put on blocks, and the entire drive mechanism can be taken out at once, such as by removing the upper plate of the drive mechanism from the bottom of the gimbal 30.

Figure 17:
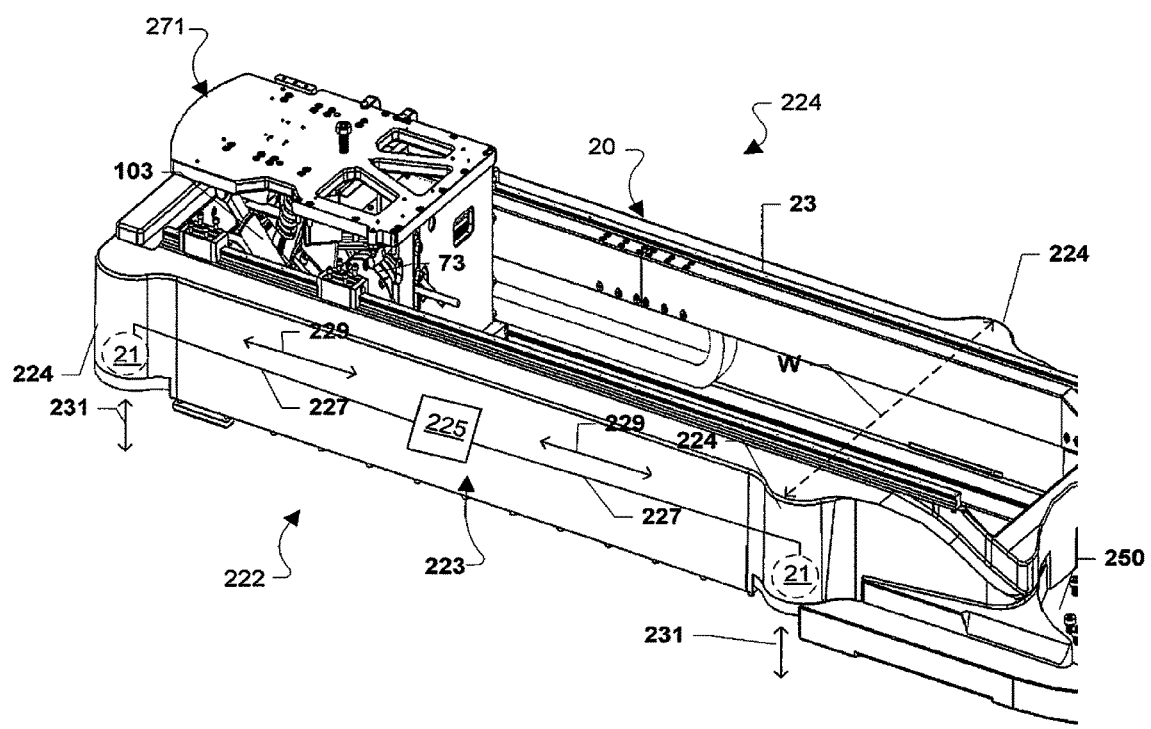
FIG. 17 illustrates a base and drive mechanism for mobile apparatus according to a second embodiment.

A drive mechanism 271 according to another embodiment is shown in FIG. 17. The drive mechanism 271 may be similar to the drive mechanism 71 described and illustrated previously in this document. The drive mechanism 271 may be located within an opening of a base 20. An apparatus, such as a medical device (e.g., a diagnostic imaging device, such as an x-ray CT scanner or MRI device) may be mounted to the top surface of the drive mechanism 271. In embodiments, the drive mechanism 271 may be mounted to a gimbal 30 and gantry 40 containing imaging components, as described above, and may support the weight of the gimbal 30 and gantry 40. The drive mechanism 271 may include a main drive wheel, such as wheel 71 described and illustrated previously in this embodiment. (The main drive wheel is not visible in FIG. 17). The drive mechanism 271 may include a main drive 73 (see FIGS. 7, 9, 11A-11B, 12A-12B, 14 and 16) that is coupled to and drives the main drive wheel for transporting the apparatus (e.g., imaging system). The drive mechanism 271 may also include a scan drive (not visible in FIG. 17), such as scan drive 75 described and illustrated previously in this document, that translates the drive mechanism 271 and any components mounted to the drive mechanism (such as a gimbal 30 and gantry 40) relative to the base 20. The translation may be via rails 23 on the base 20, as described above. The base 20 may be a rigid support structure (e.g., cast aluminum reinforced by a structural material, such as structural aluminum) and may include casters 21 for transport of the system when the base 20 is raised off the ground, and pockets 224 into which the casters 21 may retract when the base 20 is lowered, as described above. The base 20 may include, or have attached to it, a column area 250, which may be at one end of the base, and which may support a pedestal (i.e., patient column), such as pedestal 50 described above. Optionally, the column area 250 may be omitted, and the system, including the base, may be transported to a separate column or other support to perform an imaging scan. In such an embodiment of an imaging system, the system may be bi-directional in that the system can perform a scan from either end of the system.

The drive mechanism 271 of FIG. 17 may be different from the drive mechanism 70 described above in that a suspension drive assembly 77 may be omitted in the drive mechanism 271 of FIG. 17. The main drive wheel 71 may be connected to the drive mechanism 271 via a suspension system that enables the drive wheel 71 to extend and retract relative to the rest of the drive mechanism 271, as described above. The suspension system may include a pair of springs, such as gas springs (one spring 103 is visible in FIG. 17). The suspension system may be tuned to expect the same downward force from the components mounted to the drive mechanism 271 (e.g., the gantry 40 and gimbal 30) as the drive wheel 71 moves across the floor, so with any variation (i.e., a bump or dip in the floor) the suspension system moves up and down (similar to a car).

In addition, the system of FIG. 17 includes an active drive mechanism 223 in the base 20 that raises and lowers the base and may initiate the raising and lowering of the entire system. The drive mechanism 223 in the base 20 may be coupled to the casters 21, and may cause the casters 21 to extend and retract relative to the bottom surface of the base 20. In the embodiment shown in FIG. 17, the active drive mechanism 223 may cause the casters 21 to retract into their respective pockets 224 to lower the base 20 to the ground (e.g., during a scanning mode), and may cause the casters 21 to extend out from their respective pockets 224 to raise the base 20 from the ground (e.g., during transport mode). The suspension system of the drive mechanism 271 may be tuned to follow the position of the base 20. For example, as the base 20 is raised off the ground, it may push against the gimbal 30/gantry 40 assembly (i.e., making this assembly appear lighter to the suspension system of the drive mechanism 271), and the suspension system may be tuned to react to this by extending the drive wheel 71 relative to the drive mechanism 271 (i.e., so that the drive mechanism 217 and gimbal 30/gantry 40 assembly are raised up from the drive wheel 71, which maintains contact with the ground). Thus, the entire system may be raised from the ground, with the casters 21 supporting the majority of the weight (e.g., more than 50% to 100%, such as 90% or more) of the base 20 and any components mounted to the base 20 (such as a pedestal and/or patient support/table), and the drive wheel 71 supporting the majority of the weight (e.g., more than 50% to 100%, such as 90% or more) of the drive mechanism 217 and any components mounted to the drive mechanism (such as a gimbal 30 and gantry 40, including imaging components).

Similarly, as the base 20 is lowered to the ground via the active caster drive mechanism 223, the components mounted to drive mechanism 271 (e.g., gimbal 30/gantry 40 assembly) appear heavier to the suspension system of the drive mechanism 271, and the suspension system may be tuned to react to this by retracting the drive wheel 71 relative to the drive mechanism 271 (i.e., so that the drive mechanism 217 and gimbal 30/gantry 40 assembly are lowered towards the ground in conjunction with the lowering of the base 20). Thus, the entire system may be lowered to the ground, with the base 20 being supported by the ground and the drive wheel 71 supporting the majority of the weight (e.g., more than 50% to 100%, such as 90% or more) of the drive mechanism 217 and any components mounted to the drive mechanism (such as gimbal 30 and gantry 40).

Thus, in the drive mechanism 271 of FIG. 17, a separate suspension drive assembly 77 for actively extending and retracting the drive wheel 71 relative to the drive mechanism 271 may be omitted.

The active drive mechanism 223 for extending/retracting the casters 21 may be any suitable mechanism for deploying and retracting the casters 21. In some embodiments, the structure of the base 20 or overall system requirements may impose limitations on the design of the caster drive mechanism. For example, in an imaging system, such as a diagnostic (e.g., CT) imaging system, the height dimension of the base may be limited to a certain amount to ensure that the center of the imaging area (e.g., isocenter of gantry 40) is at a certain height convenient to patients and/or medical personnel. For example, the center of the imaging area may need to be at a height of about 42 inches when the system is lowered, which may limit the height of the base to being less than a foot, such as about 5-8 inches. It may also be desirable to provide a drive mechanism that fits within a compact space to help decrease the overall size and footprint of a mobile apparatus.

One embodiment of an active drive system 223 for extending/retracting the casters 21 shown in FIG. 17 includes at least one drive mechanism 225 (e.g., a motor) that is mechanically coupled to one or more casters 21 via a linkage assembly 227. The drive mechanism 225 and linkage assembly 227 may be located within the base 20. Each caster 21 may have a separate drive mechanism 225 connected to it (e.g., one drive mechanism 224 and linkage assembly 227 for each caster 21 of the system). Alternatively, a single drive mechanism 224 may be connected to multiple casters 21, including all casters 21 of the system, via suitable linkages. In the embodiment of FIG. 17, a first drive mechanism 225 is connected to two casters 21 on a first side 222 of the base 20 via linkages 227, and a second drive mechanism (not shown in FIG. 17) is connected to two casters on the second side 224 of the base 20 via linkages.

The drive mechanism 225 may be operable to impart a motive force to one or more casters 21 via the linkage assembly 227 to cause the casters 21 to extend or retract relative to the base 20. In some embodiments, such as shown in FIG. 17, the drive mechanism 224 may impart a force primarily along the length of the base (e.g., along the direction of arrow 229), and the linkage assembly 227 may convert the force into a primarily vertical force (e.g., along the direction of arrow 231) to push up or down on the casters 21 to extend and retract the casters 21 relative to the base 20.

The caster drive system 223 can use one or more of a lead screw, a ball screw, hydraulics, pneumatics or any other method or component to push up and down on the casters 21.

Figure 18:
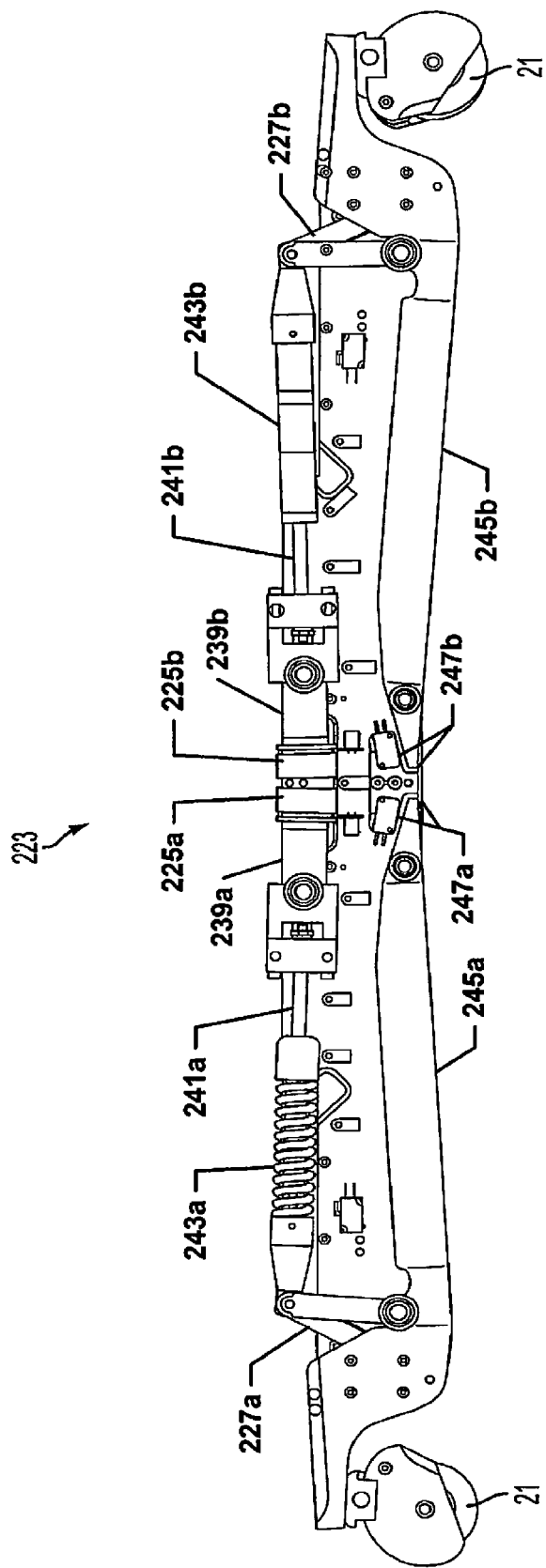
FIG. 18 illustrates a caster drive system.

An exemplary embodiment of a caster drive system 223 is shown in FIG. 18. The caster drive system 223 may be located within one side of the base 20, and a separate drive system 223 may be located in the opposite side of the base 20. The caster drive system 223 in this embodiment includes a pair of motors 225a, 225b that each rotate a lead screw 241a, 241b through a gearbox 239a, 239b, and each lead screw goes into a nut that drives a suspension system 243a, 243b (e.g., a spring suspension). In this embodiment, the suspension system 243a on the left is a different type of suspension system than the one on the right 243b due to variations in the weight supported at either end of the base 20. For example, one end of the base 20 may support a pedestal (column) and patient table, and may thus require a suspension system with a comparatively higher spring rate. The springs for the suspension system may be, for example, steel springs, polyurethane springs, gas springs, etc.

Figure 19C:
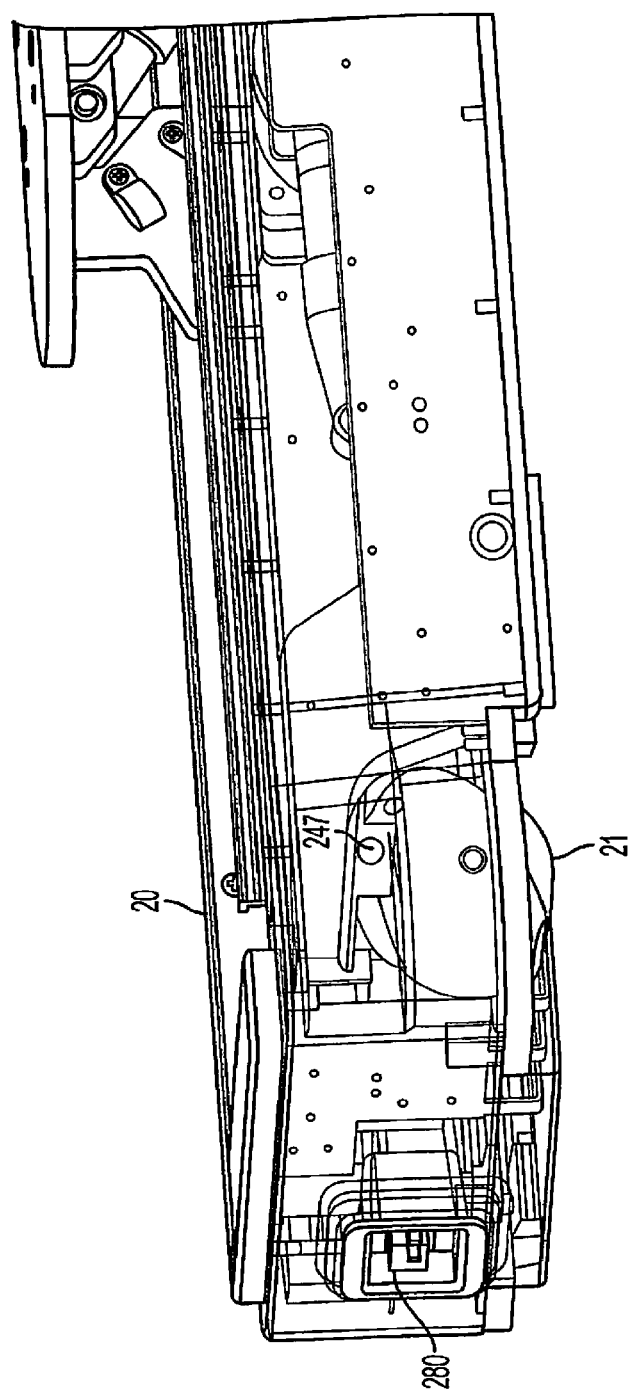
FIG. 19C illustrates the caster system of FIG. 19A with casters fully retracted.

In the embodiment of FIG. 18, each caster 21 gets pushed down via the respective suspension system, deployment linkage(s) 227a, 227b and a pivoting caster arm assembly 245a, 245b when the motor 225a, 225b rotates the lead screw 241a, 241b in a first direction. The casters 21 get pulled up when the motor 225a, 225b rotates the lead screw 245a, 245b in the opposite direction. Limit switches 247a, 247b may be provided to determine when the caster 21 is fully extended/retracted, and thus stop the motor 225a, 225b. The caster drive system 223 may also provide additional structural support within the base 20 and may help stiffen the base 20. An example of a caster 21 being retracted into a pocket 224 of a base 20 using a caster drive mechanism 223 is shown in FIGS. 19A-C. The process may be reversed (i.e., the caster 21 may be extended from base 20) using the drive mechanism 223.

A caster drive mechanism 223 such as described herein may be used for lifting and lowering any mobile apparatus. If the apparatus is light enough, all or part of the main drive 271 may be omitted, and the entire apparatus may be pushed on the casters 21.

FIG. 19A illustrates a caster 21 in a fully extended position. The caster 21 includes a wheel 241 mounted to a fork 243 having a central wheel axis 253, and a swivel joint 245 mounted to the fork 243 that enables the wheel 241 and fork 243 to rotate about a swivel axis 251 relative to the base 20. This design may enable the wheel 241 to roll in any direction, and facilitates moving the system in any direction without changing its orientation. The caster 21 typically includes an offset between the wheel axis 253 and the swivel axis 251. When the caster is moved and the wheel is not facing the correct direction, the offset causes the wheel assembly to rotate around the swivel axis 251 to follow behind the direction of movement. If there is no offset, the wheel will not rotate if not facing the correct direction. The offset distance between wheel axis 253 and swivel axis 251 determines the radius over which the caster 21 may rotate relative to the system.

The size of the caster wheels 241 may reflect a tradeoff between providing a compact system with a small footprint, and the requirements of the system. To minimize the size of the system, smaller wheels 241 may be preferred, however a certain minimum wheel size may be required for practical or regulatory reasons. For a mobile imaging system, for example, the wheels may need to have a minimum size for ease of transport in the intended environment (e.g., to get over door jams, gaps in elevators, etc.). In various embodiments, the wheel 241 may have a 3" diameter.

For certain mobile system, it may be advantageous to minimize the width of the system base. In the case of a mobile diagnostic (e.g., x-ray CT imaging) system as described above, it may be advantageous that the base not be significantly wider than the patient table to enable easy access to the patient, and in some cases, it may be desirable for the base to have a width that is less than the width of the patient table to provide a "toehold" area for medical personnel working over the patient table.

As shown in FIG. 17, the widest point of the base 20 (indicated by arrow, W), may be in the area of the "pockets" 224 into which the casters 21 are retracted. The size of the pocket required to receive the casters 21 within the base 20 so that the base may be lowered to the ground is a function of the size of the caster wheel, as well as the offset between the wheel axis and the swivel axis (i.e., the swivel radius of the caster). The larger the offset, the larger the swivel radius of the caster 21 and the larger the dimensions (e.g., diameter) of the pocket 224.

In various embodiments, a retractable and extendable caster system is provided in which at least one dimension of the space (e.g., pocket 224) in the base 20 into which the caster 21 is retracted may be minimized by providing a pivot point 247 on the caster 21 that enables the wheel assembly to pivot with respect to axis 255. The pivot point 247 may be configured to pivot the wheel assembly to reduce the offset distance between the wheel axis 253 and the swivel axis 251 as the caster 21 is pulled up into its respective pocket (e.g., the base 20 is lowered to the ground). The pivot point 247 may further enable the wheel assembly to pivot out to increase the offset distance between the wheel axis 253 and the swivel axis 251 as the caster is extended out from its respective pocket (e.g., the base 20 is raised off the ground).

In one embodiment, shown in FIGS. 19A-C, the caster 21 may be retracted relative to the base 20 until a portion 273 of the caster 21 contacts against a lip 257 of the pocket 224 (FIG. 19B). Both the lip 257 and the caster portion 273 may be made of a durable material that provides a relatively low friction interface so that the caster portion 273 may slide past the lip 257. As the caster 21 moves past the lip 257, the lip 257 pushes against the caster portion 273, causing the caster 21 to rotate on pivot point 247. FIG. 19C shows the caster 21 in fully retracted position. The caster 21 has been rotated on pivot point 247 to reduce the offset distance between the wheel axis and the swivel axis. In this example, the wheel axis is almost directly beneath the swivel axis when the caster 21 is in the retracted position. The caster 21 may fit into a pocket having smaller dimensions, which may help in providing a small, compact device.

This embodiment can be used for any mobile apparatus attached to a moveable base structure, such as mobile medical devices (e.g., diagnostic, imaging, surgical or other treatment devices), non-medical testing and imaging equipment, laboratory equipment, industrial equipment, transportation devices, information technology (IT) equipment, cargo, shipping, storage and transport equipment, and the like.

FIG. 19C illustrates a port 280 which may be used carry power into the base 20 and to the rest of the system, as well as to carry data (e.g., via an Ethernet connection) between the system and an outside entity. In the case of a mobile imaging scanner, it may be advantageous to include port(s) connecting the system to external entities in the base 20, which is the only component that is stationary during a scan.

The cables carrying power and data to and from various points in the system must then pass through the base 20 to get to port 280. However, since space in the base 20 is extremely limited, managing the power and data connections in the base can be challenging.

Figure 20A:
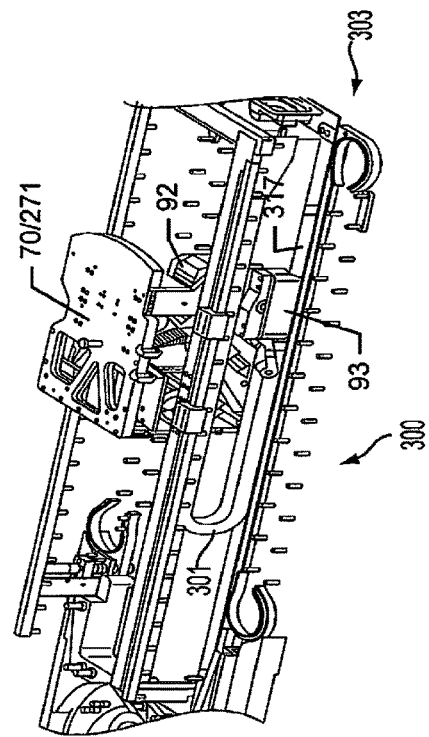
FIGS. 20A-C illustrates a cable management system for a base with the base not shown for clarity.
Figure 20B:
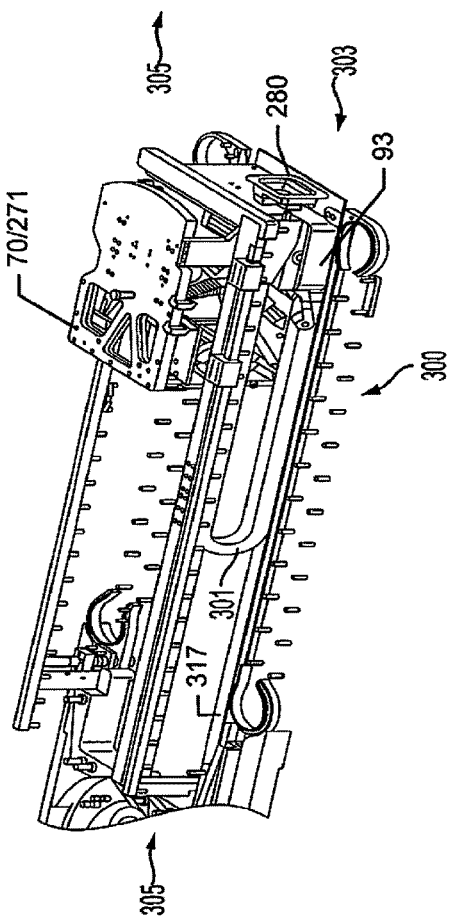
Figure 20C:
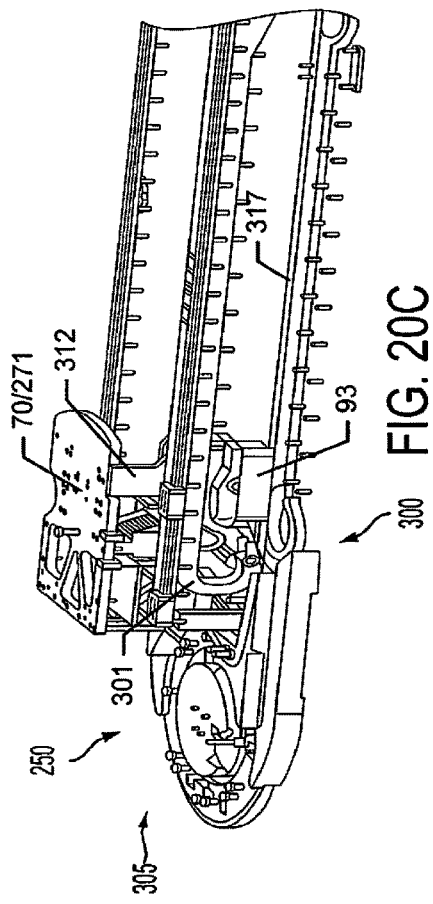
Figure 21A:
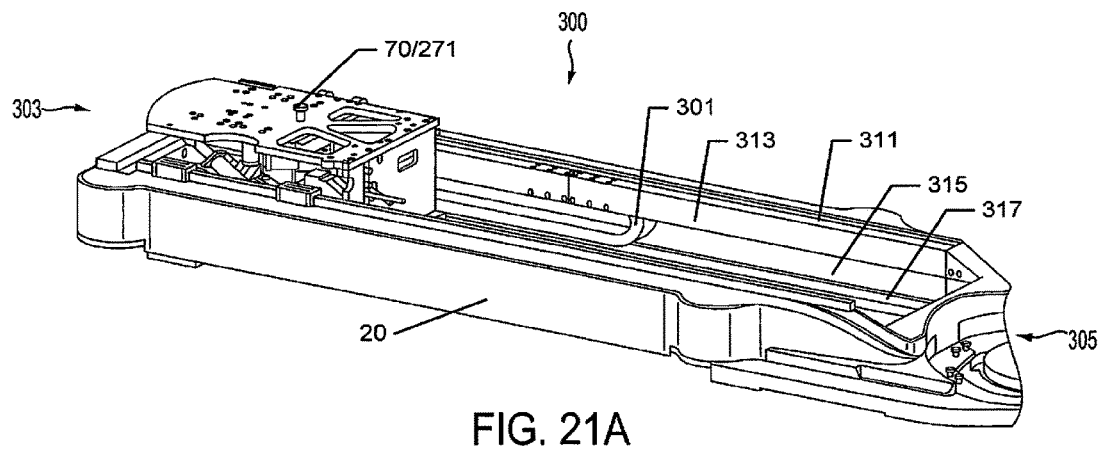
FIGS. 21A-C illustrate the cable management system with the base shown.
Figure 21B:
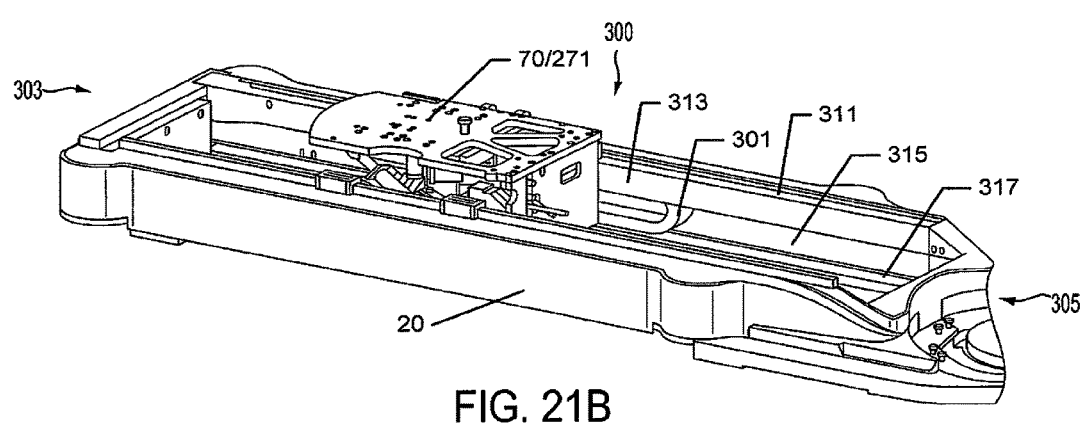
Figure 21C:
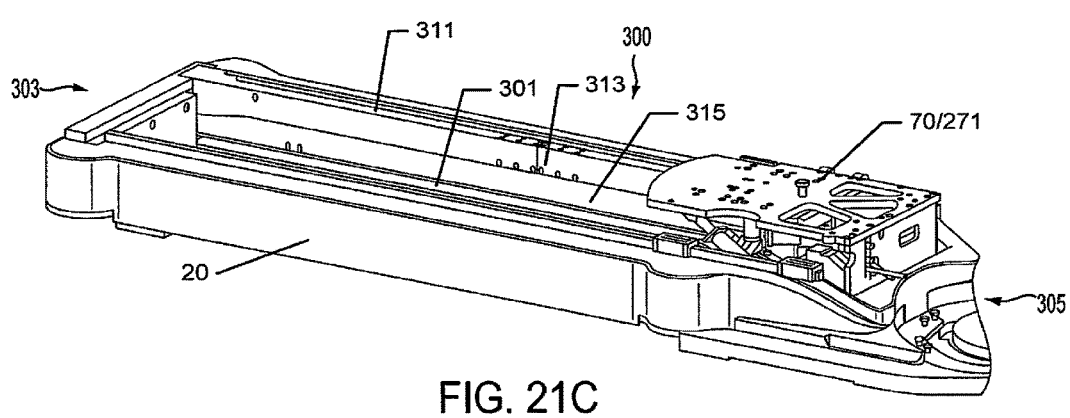

FIGS. 20A-C and 21A-C illustrates a method of cable management in the base 20. FIGS. 20A-C illustrate the cable management system 301 with the drive mechanism 70/271 in a first position in FIG. 20A (at a first end 303 of the base 20 proximate a power/data port 280), at a second position in FIG. 20B (in the middle of the base 20, or "transport" position), and at a third position in FIG. 20C (at the opposite end 305 of the base, proximate a mounting area 250 for a pedestal/column). For clarity, the base 20 is not shown in FIGS. 20A-C. FIGS. 21A-C illustrate the cable management system 301 with the drive mechanism 70/271 in the same positions as in FIGS. 20A-C, respectively, but from the opposite side and with the base 20 shown.

As shown in these drawings, the cable management system 300 may include a cable chain 301 that houses a plurality of cables. The cables may carry power and/or data between two sub-assemblies of a system, such as between the base 20 and the drive mechanism 70, 271 and a gimbal 30/gantry 40 sub-assembly of a mobile CT scanner as described above, where one sub-assembly may move relative to the other. One end of the cable chain 301 may be fixed to the base, and the other end of the cable chain 301 may be fixed to a movable component (e.g., drive mechanism 70/271). The cables and cable chain 301 may be located within a housing in the base 20, and may be protected by a structural cover 311 (see FIGS. 21A-C), such as a sheet metal cover, that may prevent the cables from getting stepped on or otherwise damaged. A splash guard 313 (see FIGS. 21A-C) may prevent liquids from getting into the housing.

The housing may also contain bearing surface 317 of the base that mates with the belt drive 93 of the drive mechanism 70/271 (i.e., Z-drive) in order to effect the translation of the drive mechanism, gimbal and gantry ring relative to the base (see FIGS. 3, 5, 8, and 10, above). A belt 94 (see FIGS. 8 and 10) may be secured to the bearing surface 317 and may be looped through the belt drive 93, where it meshes with a pulley driven by the scan drive motor 92, as shown in FIGS. 8 and 10. The rotation of the scan drive motor 92 thus causes the scan drive assembly 75 (see FIGS. 8 and 10) to traverse over the bearing surface 317 along the length of the belt 94, and thereby translate the gantry 40, gimbal 30 and drive mechanism 70/271 (which include a bracket member 312 that connects the scan drive assembly 75 to the rest of the drive mechanism 70/271 as shown in FIG. 20C) relative to the base 20. The belt drive 93 can be servo-controlled, with a linear encoder device, and have substantially zero or minimal backlash, to provide precise, controlled fine-scanning of the imaging components relative to the base and patient support table.

One end of the cable chain 301 may connect to the drive mechanism 70/271, such as at the belt drive 93 of the drive mechanism, as described above. A small gap 315 in the housing (see FIGS. 21A-C) may enable cables to connect the rest of the drive mechanism 70/271 and up into the gimbal 30 and gantry 40.

The cable chain 301 may be a flexible covering (e.g., plastic covering) that forms a loop within the housing. The cable chain 301 may form a loop as shown in FIG. 20A, with a first portion of the cable chain 301 fixed to the base 20 extending along the top interior surface of the housing, and a second portion, fixed to the drive mechanism 70/271, extending along the bottom interior surface of the housing (e.g., lying over the belt 94 for the z-drive, as described above). As the drive mechanism 70/271 translates along the base 20, the leading edge of the cable chain 301 loop is configured to travel at a lower speed than the drive mechanism (e.g., ~½ the speed of the drive mechanism translation). The second portion of the cable chain 301 gets pushed up to the top of the housing in advance of the belt drive 93 of the drive mechanism 70/271. At the end of travel (FIG. 20C) substantially all of the cable chain 301 extends along the top interior surface of the housing. The process may repeat in reverse as the drive mechanism translates in the opposite direction.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below. The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A mobile imaging system, comprising:
  a base having a housing;
  a caster coupled to the base that extends from and retracts into the housing, the caster comprising a wheel defining a wheel axis, a swivel joint defining a swivel axis, and a pivot point defining a pivot axis, where the wheel is pivotable about the pivot axis with respect to the swivel joint to change an offset distance between the wheel axis and the swivel axis;
  a first drive mechanism that moves the entire mobile imaging system in a transport mode and translates at least one imaging component relative to the base in a scan mode; and
  a second drive mechanism that extends the caster from the housing in the base to raise the base off the ground, and retracts the caster relative to the base to lower the base to the ground, the wheel pivots about the pivot axis with respect to the swivel joint to decrease the offset distance between the wheel axis and the swivel axis as the caster is retracted into the housing of the base and the wheel pivots about the pivot axis with respect to the swivel joint to increase the offset distance between the wheel axis and the swivel axis as the caster is extended from the housing of the base wherein the second drive mechanism comprises a motor coupled to an actuator that drives the extension and retraction of the caster by generating a motive force in a longitudinal direction substantially along a length of the base, and a linkage apparatus that translates the motive force to a substantially vertical force that extends and retracts the caster.

2. The mobile imaging system of claim 1, wherein the base comprises a plurality of housings and the mobile imaging system further comprises a plurality of casters coupled to the base, each caster of the plurality of casters are extended from, and retracted into, a respective housing of the plurality of housings in the base.

3. The mobile imaging system of claim 2, wherein the base comprises a central opening and the first drive mechanism is located within the central opening, and the at least one imaging component is located in a gantry that is mounted above the first drive mechanism, and the weight of the gantry and at least one imaging component is supported by the drive mechanism during the transport mode and the scan mode.

4. The mobile imaging system of claim 3, wherein the first drive mechanism comprises a main drive geared into a drive wheel and a suspension system coupled between a first portion of the first drive mechanism and the drive wheel, and the suspension system is tuned to expect a given downward force on the drive wheel from components of the system that are supported by the drive wheel.

5. The mobile imaging system of claim 4, wherein the suspension system raises the first portion of the first drive mechanism, the gantry and the at least one imaging component away from the drive wheel in response to the second drive mechanism extending the plurality of casters from the respective housings in the base.

6. The mobile imaging system of claim 5, wherein the suspension system lowers the first portion of the first drive mechanism, the gantry and the at least one imaging component towards the drive wheel in response to the second drive mechanism retracting the plurality of casters into the respective housings in the base.

7. The mobile imaging system of claim 1, further comprising a cable management system in the base that couples power and/or data between the base and at least one component that translates relative to the base.

8. The mobile imaging system of claim 7, wherein the cable management system comprises a cable chain having a first end connected to the base and a second end connected to the first drive mechanism.

9. The mobile imaging system of claim 8, wherein the cable chain is enclosed on at least three sides by the base and extends in a loop between the first and the second end, and the first drive mechanism translates relative to the base in the scan mode and a leading edge of the loop travels at a lower speed than a speed at which the first drive mechanism translates relative to the base.

10. The mobile imaging system of claim 9, wherein the base further comprises a bearing surface that mates with a scan drive of the first drive mechanism that drives the translation of the at least one imaging component relative to the base in the scan mode.

11. The mobile imaging system of claim 1, wherein the mobile imaging system is an x-ray CT imaging system.

12. The mobile imaging system of claim 1, wherein the linkage apparatus includes a caster arm longitudinally extending and pivotally coupled with a suspension linkage, the suspension linkage longitudinally extending and operatively coupled with the second drive mechanism.

13. The mobile imaging system of claim 12, wherein the second drive mechanism exerts the motive force onto and moves the suspension linkage, the suspension linkage movement pivots the position of the caster arm, raising and lowering the caster.

* * * * *